US009512216B2

(12) United States Patent
Hoffman et al.

(10) Patent No.: US 9,512,216 B2
(45) Date of Patent: *Dec. 6, 2016

(54) USE OF TNFα INHIBITOR

(71) Applicant: AbbVie Biotechnology Ltd., Hamilton (BM)

(72) Inventors: Rebecca S. Hoffman, Wilmette, IL (US); Mark Weinberg, Northbrook, IL (US); Lori K. Taylor, Boston, MA (US); Elliot K. Chartash, Marietta, GA (US); Philip Yan, Vernon Hills, IL (US); George R. Granneman, Marco Island, FL (US)

(73) Assignee: AbbVie Biotechnology Ltd., Hamilton (BM)

(*) Notice: Subject to any disclaimer, the term of this patent is extended or adjusted under 35 U.S.C. 154(b) by 0 days.

This patent is subject to a terminal disclaimer.

(21) Appl. No.: 15/173,191

(22) Filed: Jun. 3, 2016

(65) Prior Publication Data

US 2016/0272704 A1 Sep. 22, 2016

Related U.S. Application Data

(63) Continuation of application No. 14/809,828, filed on Jul. 27, 2015, which is a continuation of application No. 14/681,704, filed on Apr. 8, 2015, now Pat. No. 9,090,689, which is a continuation of application No. 14/563,056, filed on Dec. 8, 2014, now Pat. No. 9,067,992, which is a continuation of application No. 14/266,598, filed on Apr. 30, 2014, now Pat. No. 8,906,373, which is a continuation of application No. 14/228,791, filed on Mar. 28, 2014, now Pat. No. 8,808,700, which is a continuation of application No. 11/435,844, filed on May 16, 2006, now Pat. No. 8,715,664, said application No. 14/266,598 is a continuation-in-part of application No. 11/104,117, filed on Apr. 11, 2005, now Pat. No. 8,889,136.

(60) Provisional application No. 60/681,645, filed on May 16, 2005, provisional application No. 60/569,100, filed on May 7, 2004, provisional application No. 60/561,710, filed on Apr. 12, 2004, provisional application No. 60/561,139, filed on Apr. 9, 2004.

(51) Int. Cl.
- *C07K 16/24* (2006.01)
- *A61K 39/395* (2006.01)
- *A61K 9/00* (2006.01)

(52) U.S. Cl.
CPC ........... *C07K 16/241* (2013.01); *A61K 9/0019* (2013.01); *C07K 2317/21* (2013.01)

(58) Field of Classification Search
None
See application file for complete search history.

(56) References Cited

U.S. PATENT DOCUMENTS

| | | |
|---|---|---|
| 5,231,024 A | 7/1993 | Moeller et al. |
| 5,654,407 A | 8/1997 | Boyle et al. |
| 5,656,272 A | 8/1997 | Le et al. |
| 5,705,389 A | 1/1998 | Braham et al. |
| 5,795,967 A | 8/1998 | Aggarwal et al. |
| 5,859,205 A | 1/1999 | Adair et al. |
| 5,877,293 A | 3/1999 | Adair et al. |
| 5,888,511 A | 3/1999 | Skurkovich et al. |
| 5,929,212 A | 7/1999 | Jolliffe et al. |
| 5,958,953 A | 9/1999 | Marfat |
| 5,994,510 A | 11/1999 | Adair et al. |
| 6,090,382 A | 7/2000 | Salfeld et al. |
| 6,177,077 B1 | 1/2001 | Tobinick |
| 6,214,870 B1 | 4/2001 | McClure et al. |
| 6,235,281 B1 | 5/2001 | Stenzel et al. |
| 6,258,562 B1 | 7/2001 | Salfeld et al. |
| 6,270,766 B1 | 8/2001 | Feldman et al. |
| 6,372,715 B1 | 4/2002 | Kaltwasser et al. |
| 6,379,666 B1 | 4/2002 | Tobinick |
| 6,419,944 B2 | 7/2002 | Tobinick |
| 6,423,321 B2 | 7/2002 | Tobinick |
| 6,448,380 B2 | 9/2002 | Rathjen et al. |
| 6,451,983 B2 | 9/2002 | Rathjen et al. |
| 6,498,237 B2 | 12/2002 | Rathjen et al. |
| 6,509,015 B1 | 1/2003 | Salfeld et al. |
| 6,537,549 B2 | 3/2003 | Tobinick |
| 6,593,458 B1 | 7/2003 | Rathjen et al. |
| 6,747,002 B2 | 6/2004 | Cheung et al. |
| 7,012,135 B2 | 3/2006 | Athwal et al. |
| 7,070,775 B2 | 7/2006 | Le et al. |
| 7,153,507 B2 | 12/2006 | van de Winkel et al. |
| 7,192,584 B2 | 3/2007 | Le et al. |

(Continued)

FOREIGN PATENT DOCUMENTS

| | | |
|---|---|---|
| CA | 2803741 A1 | 1/2004 |
| EP | 0101681 | 3/1984 |

(Continued)

OTHER PUBLICATIONS

Adalimumab Product Approval Information—Licensing Action Dec. 31, 2002: Statistical Review.

Bhalero et al, "The genetics of psoriasis: a complex disorder of the skin and immune system," Human Molecular Genetics 7(10):1537-1545 (1998).

Clinical Trial NCT00645814, "Multicenter Study of the Safety and Efficacy of Adalimumab in Subjects With Moderate to Severe Chronic Plaque Psoriasis," (clinicaltrials.gov/ct2/show/NCT00645814, 2008), 2 pages (2003) (Tabular View).

Clinical Trial NCT00645905, "Study of Two Dosing Schedules of Adalimumab in Subjects With Moderate to Severe Chronic Plaque Psoriasis," (clinicaltrials.gov/ct2/show/NCT00645905, accessed on Oct. 29, 2015), 3 pages (2003) (Tabular View).

(Continued)

*Primary Examiner* — Ilia Ouspenski
(74) *Attorney, Agent, or Firm* — Foley Hoag LLP

(57) ABSTRACT

The invention describes methods of treating erosive polyarthritis comprising administering a TNFα antibody, or antigen-binding portion thereof. The invention also describes a method for testing the efficacy of a TNFα antibody, or antigen-binding portion thereof, for the treatment of erosive polyarthritis.

16 Claims, 9 Drawing Sheets

(56) References Cited

U.S. PATENT DOCUMENTS

| | | |
|---|---|---|
| 7,223,394 B2 | 5/2007 | Salfeld et al. |
| 7,250,165 B2 | 7/2007 | Heavner et al. |
| 7,276,239 B2 | 10/2007 | Le et al. |
| 7,276,478 B2 | 10/2007 | Sivakumar et al. |
| 7,438,907 B2 | 10/2008 | Schuurman et al. |
| 7,521,206 B2 | 4/2009 | Heavner et al. |
| 7,541,031 B2 | 6/2009 | Salfeld et al. |
| 7,588,761 B2 | 9/2009 | Salfeld et al. |
| 7,691,378 B2 | 4/2010 | Heavner et al. |
| 7,833,525 B2 | 11/2010 | Shenoy et al. |
| 7,863,426 B2 | 1/2011 | Wan et al. |
| 7,879,328 B2 | 2/2011 | Ruben et al. |
| 7,919,264 B2 | 4/2011 | Maksymowych et al. |
| 8,034,906 B2 | 10/2011 | Borhani et al. |
| 8,092,998 B2 | 1/2012 | Stuhlmuller et al. |
| 8,093,045 B2 | 1/2012 | Pla et al. |
| 8,168,760 B2 | 5/2012 | Borhani et al. |
| 8,187,836 B2 | 5/2012 | Hsieh |
| 8,197,813 B2 | 6/2012 | Salfeld et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,636,704 B2 | 1/2014 | Shang et al. |
| 8,663,945 B2 | 3/2014 | Pla et al. |
| 8,679,061 B2 | 3/2014 | Julian et al. |
| 8,715,664 B2 | 5/2014 | Hoffman et al. |
| 8,747,854 B2 | 6/2014 | Okun et al. |
| 8,753,633 B2 | 6/2014 | Salfeld et al. |
| 8,753,839 B2 | 6/2014 | Fraunhofer et al. |
| 8,808,700 B1 | 8/2014 | Hoffman et al. |
| 8,821,865 B2 | 9/2014 | Neu et al. |
| 8,846,046 B2 | 9/2014 | Kaymakcalan et al. |
| 8,883,146 B2 | 11/2014 | Fraunhofer et al. |
| 8,889,135 B2 | 11/2014 | Fischkoff et al. |
| 8,889,136 B2 | 11/2014 | Hoffman et al. |
| 8,906,373 B2 | 12/2014 | Banerjee et al. |
| 8,986,693 B1 * | 3/2015 | Hoffman .............. C07K 16/241 424/145.1 |
| 9,090,689 B1 | 7/2015 | Hoffman et al. |
| 2001/0021380 A1 | 9/2001 | Pluenneke |
| 2003/0012786 A1 | 1/2003 | Teoh et al. |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2004/0009166 A1 | 1/2004 | Filpula et al. |
| 2004/0009172 A1 | 1/2004 | Fischkoff et al. |
| 2004/0033228 A1 | 2/2004 | Krause et al. |
| 2004/0038874 A1 | 2/2004 | Omoigui |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0219142 A1 | 11/2004 | Banerjee et al. |
| 2005/0249735 A1 | 11/2005 | Le et al. |
| 2006/0018907 A1 | 1/2006 | Le et al. |
| 2006/0083741 A1 | 4/2006 | Hoffman et al. |
| 2006/0246073 A1 | 11/2006 | Knight et al. |
| 2007/0041905 A1 | 2/2007 | Hoffman et al. |
| 2007/0081996 A1 | 4/2007 | Hoffman et al. |
| 2007/0196373 A1 | 8/2007 | Le et al. |
| 2007/0202104 A1 | 8/2007 | Banerjee et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0311043 A1 | 12/2008 | Hoffman et al. |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0202557 A1 | 8/2009 | Argiriadi et al. |
| 2009/0226530 A1 | 9/2009 | Lassner et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0040630 A1 | 2/2010 | Elden et al. |
| 2010/0278822 A1 | 11/2010 | Fraunhofer et al. |
| 2011/0171227 A1 * | 7/2011 | Okun .................. C07K 16/241 424/142.1 |
| 2012/0014956 A1 | 1/2012 | Kupper et al. |
| 2012/0039900 A1 | 2/2012 | Stuhlmuller et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0243786 A1 | 9/2013 | Banerjee et al. |
| 2013/0330356 A1 | 12/2013 | Salfeld et al. |
| 2016/0176957 A1 * | 6/2016 | Hoffman .............. C07K 16/241 424/9.2 |
| 2016/0200809 A1 * | 7/2016 | Willian ............... C07K 16/241 424/142.1 |

FOREIGN PATENT DOCUMENTS

| | | |
|---|---|---|
| EP | 0186833 | 7/1986 |
| EP | 0212489 | 3/1987 |
| EP | 0 230574 A2 | 8/1987 |
| EP | 0351789 | 1/1990 |
| EP | 0366043 | 5/1990 |
| EP | 0 374 510 A1 | 6/1990 |
| EP | 0 377823 A2 | 7/1990 |
| EP | 0 453898 A2 | 10/1991 |
| EP | 0492448 | 7/1992 |
| EP | 260 610 | 9/1993 |
| EP | 0 585705 A1 | 3/1994 |
| EP | 0614984 | 9/1994 |
| EP | 0659766 | 6/1995 |
| EP | 1 232 753 A1 | 8/2002 |
| EP | 1944322 A2 | 7/2008 |
| JP | 11127882 | 5/1999 |
| JP | 2001-302542 | 10/2001 |
| WO | WO-91/02078 | 2/1991 |
| WO | WO-91/03553 A1 | 3/1991 |
| WO | WO-91/04054 A1 | 4/1991 |
| WO | WO-91/09967 A1 | 7/1991 |
| WO | WO-92/11383 | 7/1992 |
| WO | WO-92/16221 A1 | 10/1992 |
| WO | WO-92/16553 | 10/1992 |
| WO | WO-92/17583 A1 | 10/1992 |
| WO | WO-93/06213 | 4/1993 |
| WO | WO-93/11793 | 6/1993 |
| WO | WO-93/19751 A1 | 10/1993 |
| WO | WO-94/29347 | 12/1994 |
| WO | WO-95/23813 | 9/1995 |
| WO | WO-96/33204 A1 | 10/1996 |
| WO | WO-97/29131 | 8/1997 |
| WO | WO-98/04281 A1 | 2/1998 |
| WO | WO-98/05357 | 2/1998 |
| WO | WO-98/22460 | 5/1998 |
| WO | WO-98/46642 A1 | 10/1998 |
| WO | WO-00/62790 A2 | 10/2000 |
| WO | WO-01/00229 | 1/2001 |

(56) References Cited

FOREIGN PATENT DOCUMENTS

| | | |
|---|---|---|
| WO | WO-01/37874 | 5/2001 |
| WO | WO-01/43773 A1 | 6/2001 |
| WO | WO-01/62272 | 8/2001 |
| WO | WO-01/94585 | 12/2001 |
| WO | WO-02/12502 | 2/2002 |
| WO | WO-02/072636 A2 | 9/2002 |
| WO | WO-02/096461 | 12/2002 |
| WO | WO-02/100330 | 12/2002 |
| WO | WO-03/016468 A2 | 2/2003 |
| WO | WO-2004/009776 A2 | 1/2004 |
| WO | WO-2004/016286 A2 | 2/2004 |
| WO | WO-2004/037205 A2 | 5/2004 |
| WO | WO-2004/082635 A2 | 9/2004 |
| WO | WO-2004/092448 | 10/2004 |
| WO | WO-2005/110452 A2 | 11/2005 |
| WO | WO-2006/041970 | 4/2006 |

OTHER PUBLICATIONS

Clinical Trial NCT00646178, "Study of the Safety and Efficacy of Adalimumab in Subjects With Moderate to Severely Active Psoriatic Arthritis Subjects with Inadequate Response to Diesease Modifying Anti-Rheumatic Drug Therapy," (clinicaltrials.gov/ct2/show/NCT00646178, accessed on Oct. 29, 2015), 3 pages (2008) (Tabular View).
Clinical Trial NCT00646191, "Study of the Safety and Efficacy of Adalimumab in Subjects With Moderate to Severe Chronic Plaque Psoriasis," (clinicaltrials.gov/ct2/show/NCT00646191, accessed on Oct. 24, 2014), 3 pages (2008) (Tabular View).
Clinical Trial NCT00646386, "Study of the Safety and Efficacy of the Human Anti-TNF Monoclonal Antibody Adalimumab in Subjects With Moderately to Severely Active Psoriatic Arthritis," (clinicaltrials.gov/show/NCT00646386, accessed on Aug. 1, 2013), 3 pages (2003) (Tabular View).
Dermatology and Psychosomatics 4(2): 100-102 (2003).
Dermatology and Psychosomatics 4(2): 100-102 (2003)—English translation.
Dermatology and Psychosomatics 4(2): 100-102 (2003)—Information on the publication date.
Extract from British National Formulary, Mar. 2003.
Extract from European SmPC for Remicade (Oct. 4, 2005).
Extract from European SmPC for Humira (Jun. 24, 2016).
Krueger et al, "Involved and Uninvolved Skin from Psoriatic Subjects: Are they equally Diseased" J Clin Invest 68:1548-1557 (1981).
Letter dated Dec. 31, 2002 CEBR (FDA) to Abbott Laboratories.
LexisNexis—PR Newswire Assoc., Abbott Laboratories Initiates Clinical Trials to Explore Use of HUMIRA® (adalimumab) in Psoriasis and Psoriatic Arthritis, Press Release by Abbott Laboratories (Mar. 3, 2003).
Mordovtsev et al, "Morphology of Skin Microvasculature in Psoriasis," 11(1): 33-42 (1989).
Mosteller, RD "Simplified Calculation of Body-Surface Area," N Engl J Med 317(17):1098 (1987).
Pigman et al, "Sialic Acid in Normal and Arthritic Human Synovial Fluids," Arthritis & Rheumatism 1(2):151-166 (1958).
Raychadhuri et al., "Psoriasis Risk Factors: Role of Lifestyle Practices," CUTIS 66 (5):348-352 (2000).
Sakai et al., "Prognostic factor analysis for plaque psoriasis," J Invest Dermatol 121 (1):JID Abstracts, p. 58, abstract (0345).
Steiner, et al, "Cytokine production by synovial T cells in rheumatoid arthritis," Rheumatology 38:202-213 (1999).
UK High Court decision of Actavis v. Eli Lilly (Oct. 14, 2015) EWHC 3294 (pat).
"Active Pharmaceutical Ingredient Watch," Chemical Market Reporter, 11 (Mar. 2003).
"Annual Updates 2003: Dematologic Drugs," Drugs of the Future 28(2):175-209 (2003).
[Online] Statement on a Nonproprietary Name Adopted by the USAN Council: Adalimumab, [retrieved on May 19, 2011] Retrieved from: www.ama-assn.org/resources/doc/usan/adalimumab.doc, p. 1.
Abbott Laboratories, Earnings Conference Call transcript (Apr. 9, 2002).
Abbott Laboratories, Earnings Conference Call transcript (Jul. 11, 2002).
Aboulafia, "Etanercept for the treatment of human immunodeficiency virus-associated D psoriatic arthritis," Mayo Clinic Proceedings, 75(10):1093-1098 (2000).
Abraham et al., "Efficacy and Safety of Monoclonal Antibody to Human Tumor Necrosis Factor a in Patients with Sepsis Syndrome," JAMA, 273(12): 934-941 (1995).
Abraham et al., "Why immunomodulatory therapies have not worked in sepsis," Intensive Care Med, 25:556-566 (1999).
Advisory Committee Briefing Document HUMIRA (Adalimumab), Abbott Laboratories, Briefing document dated Feb. 4, 2003.
Alexander et al., "Elevated Levels of Proinflammatory Cytokines in the Semen of Patients With Chronic Prostatitis/Chronic Pelvic Pain Syndrome," Urology, 52:744 (1998).
Alonso et al., "Psoriatic Arthritis (PA): A Clinical, Immunological and Radiological Study of 180 Patients," Br. J. Rheumatol, 30:245-260 (1991).
Antoni et al., "Infliximab for psoriasis and psoriatic arthritis," Clin. Exp. Rheum., 20:S122-S125 (2002).
Antoni et al., "Open-label study of infliximab treatment for psoriatic arthritis: clinical and C2 magnetic resonance imaging measurements of reduction of inflammation," Arthritis & Rheumatism, 47(5):506-512 (2002).
Antoni et al., "Successful treatment of severe psoriatic arthritis with infliximab," Arthr. Rheum. 42(Suppl.):S371 (Abstract #1801) (1999).
Antoni, C., et al., "Successful Treatment of Psoriatic Arthritis with Infliximab in a MRI Controlled Study," Abstract OP 6.1, J. of Rheumatology, 27 (Supp. 59):24 (2000).
Asadullah et al., "A high prevalence of cytomegalovirus antigenaemia in patients with moderate to severe chronic plaque psoriasis: an association with systemic tumor necrosis factor a overexpression," Br. J. Dermatol, 141(1):94-102 (1999).
Asadullah, "Novel immunotherapies for psoriasis," 23(1):47-53 (2002).
Asakawa et al., "Effects of Cernitin Pollen-Extract (Cernilton) on Inflammatory Cytokines in Sex-Hormone Induced Nonbacterial Prostatitis Rats," Hinyokika Kiyo, 47:459-465 (2001).
Asli et al., "Inhibition of tumor necrosis factor alpha and ankylosing spondylitis," N Engl J Med, 348(4):359-61 (2003).
Awni et al., "Steady-State Pharmacokinetics (PK) of Adalimumab (HUMIRA1M, Abbott) Following 40 mg Subcutaneous (sc) Injection Every Other Week (eow) in Rheumatoid Arthritis (RA) Patients with and without Methotrexate (MTX) Background Therapy," Arthritis Rheum, 48(9):S140 (2003).
Badia et al., "Measuring health-related quality of life in patients with mild to moderate eczema and psoriasis: clinical validity, reliability and sensibility to change of the DLQI," British Journal of Dermatology, 141:698-702 (1999).
Baeten et al., "Immunomodulatory effects of anti-tumor necrosis factor alpha therapy on synovium in spondylarthropathy: histologic findings in eight patients from an open-label pilot study," Arthritis & Rheumatism, 44(1):186-195 (2001).
Bain et al., "Adalimumab," Nat. Rev. Drug Disc., 2(9):693-694 (2003).
Bang et al., "Adalimumab: a review of its use in rheumatoid arthritis," BioDrugs, 18(2):121-139 (2004).
Bansback et al., "Cost effectiveness of adalimumab in the treatment of patients with moderate to severe rheumatoid arthritis in Sweden," Annals of the Rheumatic Diseases, 64(7):995-1002 (2005).
Bansback et al., "The Cost Effectiveness of Adalimumab (HUMIRA™, Abbott) in the Treatment of Patients with Moderate to Severe Rheumatoid Arthritis (RA)," Arthritis Rheum, 48(9):S611 (2003).

(56) References Cited

OTHER PUBLICATIONS

Barbuto et al., "Production of Neutralizing Antibodies to Tumor Necrosis Factor by Human Tumor-Infiltrating B Lymphocytes," Proc. Am. Assoc. Cancer Res, 34(487) Abstr. 2904 (1993).

Barrera et al., "Drug survival, efficacy and toxicity of monotherapy with a fully human anti-tumour necrosis factor-a antibody compared with methotrexate in long-standing rheumatoid arthritis," Rheumatology, 41:430-439 (2002).

Barrera et al., "Effect of a Fully Human Anti-TNFa Monoclonal Antibody on the Local and Systemic Expression of TNFa and IL-113," Arthritis Rheum, 42(9):S75 (1999).

Barrera et al., "Effects of treatment with a fully human anti-tumour necrosis factor a monoclonal antibody on the local and systemic homeostasis of interleukin 1 and TNFa in patients with rheumatoid arthritis," Ann. Rheum Dis., 60:660-669 (2001).

Bathon et al., "A Comparison of Etanercept and Methotrexate in Patients with early Rheumatoid Arthritis," N Engl J Med., 343(22):1586-93 (2000).

Baugh et al., "Mechanisms for modulating TNFa in immune and inflammatory disease," Current Opinion in Drug Discovery & Development, 4(5):635-650 (2001).

Beers et al., "Inflammatory Bowel Diseases," The Merck Manual of Diagnosis and Therapy, 17(31):302-313 (1999).

Beers et al., "Juvenile rheumatoid arthritis," The Merck Manual of Diagnosis and Therapy, 17(270):2402-2403 (1999).

Bendtzen et al., "Auto-antibodies to IL-1a and TNFa in Normal Individuals and in Infectious and Immunoinflammatory Disorders," The Physiological and Pathological Effects of Cytokines, 447-452 (1990).

Bennett, A.N. et al., "Adalimumab in clinical practice. Outcome in 70 rheumatoid arthritis patients, including comparison of patients with and without previous anti-TNF exposure," Rheumatology, 44:1026-1031 (2005).

Billiau et al., "Infliximab for systemic onset juvenile idiopathic arthritis: experience in 3 children," Journal of Rheumatology, 29(5):1111-1114 (2002).

Biotech Week, "Cambridge Antibody Technology; Cambridge Antibody reports interim results on several trials" (Jun. 19, 2002).

Bodmer et al., "Preclinical review of anti-tumor necrosis factor monoclonal antibodies," Critical Care Medicine, 21(10):S441-S446 (1993).

Boeger et al., "Treatment of ankylosing spondylitis with infliximab," Ann Rheum Dis., 60(12):1159-1160 (2001).

Boekstegers et al., "Repeated administration of a F(ab')2 fragment of an anti-tumor necrosis factor alpha monoclonal antibody in patients with severe sepsis: effects on the cardiovascular system and cytokine levels," Shock, 1(4):237-245 (1994).

Bombardier et al., "Pattern of DMARD use in a North American Cohort of Patients with Early Rheumatoid Arthritis (RA) (SONORA)," Arthritis Rheum, 46(9):S344 (2002).

Borigini et al., "Innovative Treatment Approaches for rheumatoid arthritis. Combination Therapy," Bailliere's Clinical Rheumatology, 9(4):689-710 (1995).

Boyle et al., "A Novel Monoclonal Human IgM Autoantibody which Binds Recombinant Human and Mouse Tumor Necrosis Factor-a," Cell. Immunol, 152:556-68 (1993).

Boyle et al., "The B5 Monoclonal Human Autoantibody Binds to Cell Surface TNFa on Human Lymphoid Cells and Cell Lines and Appears to Recognize a Novel Epitope," Cell. Immunol., 152:569-81 (1993).

Brandt et al., ""Experimentelle Therapie" bei entzündlichen Wirbelsäulenerkrankungen," Morbus Bechterew Journal, 1:81 (2000).

Brandt et al., "Successful short term treatment of severe undifferentiated spondyloarthropathy with the anti-tumor necrosis factor-alpha monoclonal antibody infliximab," J Rheumatol, 29(1):118-122 (2002).

Brandt et al., "Successful treatment of active ankylosing spondylitis with the anti-tumor necrosis factor alpha monoclonal antibody infliximab," Arthritis Rheum, 43(6):1346-1352 (2000).

Braun et al., "Anti-TNFalpha: a new dimension in the pharmacotherapy of the spondyloarthropathies!?" Ann Rheum Dis, 59(6):404-6 (2000).

Braun et al., "Anti-tumour necrosis factor alpha therapy for ankylosing spondylitis: international experience," Ann Rheum Dis, 61(3):iii51-iii60 (2002).

Braun et al., "Biologic therapies in the spondyloarthritis: new opportunities, new challenges," Curr Opin Rheumatol, 15(4):394-407 (2003).

Braun et al., "International ASAS consensus statement for the use of anti-tumour necrosis factor agents in patients with ankylosing spondylitis," Ann Rheum Dis, 62(9):817-24 (2003).

Braun et al., "New treatment options in spondyloarthropathies: increasing evidence for significant efficacy of anti-tumor necrosis factor therapy," Curr Opin Rheumatol, 13(4):245-9 (2001).

Braun et al., "Novel approaches in the treatment of ankylosing spondylitis and other spondyloarthritides," Expert Opin Investig Drugs, 12(7):1097-109 (2003).

Braun et al., "Role of Novel Biological Therapies in Psoriatic Arthritis," BioDrugs 17(3):187-199 (2003).

Braun et al., "Therapy of ankylosing spondylitis and other spondyloarthritides: established medical; treatment anti-TNF-a therapy and other novel approaches," Arthritis Research, 4:307-321 (2002).

Braun et al., "Treatment of active ankylosing spondylitis with infliximab: a randomized controlled multicentre trial," Lancet, 659(9313):1187-93 (2002).

Breban et al., "Efficacy of infliximab in refractory ankylosing spondylitis: results of a six-month open-label study," Rheumatology, 41(11):1280-1285 (2002).

Breedveld et al., "Sustained Efficacy Over 4 Years with Adalimumab in Patients with Active Rheumatoid Arthritis," Ann. Rheum. Dis, 62(1):169 (2003).

Breedveld et al., "Sustained Efficacy over 5 Years with Adalimumab (HUMIRA®) in Patients with Active Rheumatoid Arthritis," Arthritis Rheum, 48(9):S118 (2003).

Breedveld et al., "The Fully Human Anti-TNF Antibody Adalimumab (D2E7) in Combination with Methotrexate (MTX) in the Treatment of Active Rheumatoid Arthritis: Results of a 2-Year Study," EULAR, Prague, Czech Republic (2001).

Breedveld et al., "The Long-term Efficacy and Safety of Adalimumab (D2E7), the Fully Human Anti-TNF Monoclonal Antibody, in Combination with Methotrexate in the Treatment of Rheumatoid Arthritis: Results of a 2-Year Study," JCR, 8(3):S46 (2002).

Brekke et al., "Therapeutic Antibodies for Human Diseases at the Dawn of the Twenty-first Century," Nat Rev Drug Discov., 2(3):240 (2003).

Brisby et al., "Proinflammatory cytokines in cerebrospinal fluid and serum in patients with disc herniation and sciatica", Eur Spine J., 11:62-66 (2002).

Brocq et al., "Adalimumab in rheumatoid arthritis after failed infliximab and/or etanercept therapy: experience with 18 patients," Joint Bone Spine, 71:601-603 (2004).

Burmester et al., "Effect of Dose Interruptions on the Efficacy and Safety of Adalimumab in Patients with RA," Ann. Rheum. Dis., 62(1):192 (2003).

Burmester et al., "Long-Term Efficacy and Safety of Adalimumab (D2E7) Monotherapy in Patients With DMARD-Refractory Rheumatoid Arthritis—Results From a 2-Year Study," Arthritis Rheum, 46(9):S537 (2002).

Burmester et al., "Sustained Efficacy of Adalimumab Monotherapy for More than Four Years in DMARD-Refractory RA," Ann. Rheum. Dis., 62(1):192-3 (2003).

Callen et al., "Adalimumab effectively controlled recalcitrant generalized pustular psoriasis in an adolescent," J. Dermatol. Treat. 16:350-352 (2005).

Canadian Coordinating Office for Health Technology Assessment, "Emerging Drug List: Adalimumab and Rheumatoid Arthritis," No. 42, available at https://www.cadth.ca/media/pdf/108_No42_adalimumab_edrug_e.pdf (2003).

(56) References Cited

OTHER PUBLICATIONS

Carlin et al., "A 50% reduction in the psoriasis area and severity index (PASI.50) is a clinically significant endpoint in the assessment of psoriasis," Journal of the American Academy of Dermatology, 50(6): 859-866 (2003).
Case, "Old and New Drugs Used in Rheumatoid Arthritis: A Historical Perspective," American Journal of Therapeutics, 8:163-179 (2001).
Casset et al., "A peptide mimetic of an anti-CD4 monoclonal antibody by rational design," Biochemical and Biophysical Research Communications, 307:198-205 (2003).
Cauza et al., "Treatment of psoriatic arthritis and psoriasis vulgaris with the tumor necrosis factor inhibitor infliximab," Rheumatol Int. 22:227-232 (2002).
Cavagna et al., "Infliximab in the treatment of adult Still's disease refractory to conventional therapy," Clin Exp Rheumatol, 19(3):329-332 (2001).
Cella, "Validation of the Functional Assessment of Chronic Illness Therapy-Fatigue (FACITF) in the Safety Trial of Adalimumab (D2E7) in Rheumatoid Arthritis (STAR)," Arthritis Rheum, 46(9):S115 (Abst 208) (2002).
Challener, Cynthia, "Biotechnology drugs offer fertile ground for API producers," Chemical Market Reporter 260(13):FR3-FR12 (2001).
Chartash et al., "Adalimumab Improves Fatigue in Patients with Active Rheumatoid Arthritis," Ann. Rheum. Dis., 62(1):349 (2003).
Chaudhari et al., "Efficacy and safety of infliximab monotherapy for plaque-type psoriasis: a randomized trial," Lancet, 357(9271):1842-7 (2001).
Chen et al., "Adalimumab efficacy and safety in patients with moderate to severe chronic plaque psoriasis: preliminary findings from a 12-week dose-ranging trial," Supplement to the J. Am. Acad. of Dermatol, 50(3): P2 (2004).
Cherouvim et al., "Infliximab Therapy for Patients With Active and Refractory Spondyloarthropathies at the Dose of 3 mg/kg," J. Clin. Rheumatol., 10:162-168 (2004).
Chew et al., "Successful treatment of severe psoriasis and psoriatic arthritis with adalimumab," Brit J Derm, 151(2):492-496 (2004).
Chikanza, "Juvenile rheumatoid arthritis: therapeutic perspectives," Pediatric Drugs 4(5):335-348 (2002).
Chow et al., "Effect of monoclonal antibody on human tumor necrosis factor (TNF MAb) on NFa, IL-113. and IL-6 levels in patients with sepsis syndrome," Clinical Research, 42(2): 299A (1994).
Clinical Trial NCT00645814, "Multicenter Study of the Safety and Efficacy of Adalimumab in Subjects With Moderate to Severe Chronic Plaque Psoriasis," (clinicaltrials.gov/ct2/show/NCT00645814, 2008), 2 pages (2003).
Clinical Trial NCT00645905, "Study of Two Dosing Schedules of Adalimumab in Subjects With Moderate to Severe Chronic Plaque Psoriasis," (clinicaltrials.gov/ct2/show/NCT00645905, accessed on Oct. 29, 2015), 3 pages (2003).
Clinical Trial NCT00646178, "Study of the Safety and Efficacy of Adalimumab in Subjects With Moderate to Severely Active Psoriatic Arthritis Subjects with Inadequate Response to Diesease Modifying Anti-Rheumatic Drug Therapy," (clinicaltrials.gov/ct2/show/NCT00646178, accessed on Oct. 29, 2015), 3 pages (2008).
Clinical Trial NCT00646191, "Study of the Safety and Efficacy of Adalimumab in Subjects With Moderate to Severe Chronic Plaque Psoriasis," (clinicaltrials.gov/ct2/show/NCT00646191, accessed on Oct. 24, 2014), 3 pages (2008).
Clinical Trial NCT00646386, "Study of the Safety and Efficacy of the Human Anti-TNF Monoclonal Antibody Adalimumab in Subjects With Moderately to Severely Active Psoriatic Arthritis," (clinicaltrials.gov/show/NCT00646386, accessed on Aug. 1, 2013), 3 pages (2003).
Cohen et al., "Intersept: An international, multicenter, placebo-controlled trial of monoclonal antibody to human tumor necrosis factor-a in patients with sepsis," Crit Care Med., 24(9):1431-1440 (1996).
Colman, "Effects of amino acid sequence changes on antibody-antigen interactions," Research in Immunology, 145(1):33-36 (1994).
Commission Decision of Sep. 8, 2003 granting marketing authorization for Humira® Adalimumab.
Corluy, "Clinical Response Compared to DAS28 and ACR-Response Criteria in Rheumatoid Arthritis Patients on Infliximab," EULAR, abstract (2002).
Costello, "A New Era in Rheumatoid Arthritis Treament," Wisconsin Medical Journal 102(7):29-33 (2003).
Cox et al., "A directory of human germ-line V segments reveals a strong bias in their usage," Eur. J. Immunol., 24(2):827-36 (1994).
Cush, "Infliximab (Remicade) Approved for Use in Rheumatoid Arthritis," American College of Rheum, (2000).
D'Haens et al., "Etanercept in Treatment of Active Refractory Crohn's Disease: A Single-Center Pilot Trial," J. Am. Gastroenterol, 118:2564-2568 (2001).
Davison et al., "Etanercept for severe psoriasis and psoriatic arthritis: observations on combination therapy," British Journal of Dermatology, 147(4):831-2 (2002).
Dayer et al., "Anti-TNF-alpha therapy for ankylosing spondylitis—a specific or nonspecific treatment?" N Engl J Med, 346(18):1399-400 (2002).
De Keyser et al., "Anti-TNF-alpha therapy in ankylosing spondylitis," Cytokine, 33:294-298 (2006).
Den Broeder et al., "A Single Dose, Placebo Controlled Study of the Fully Human Anti-Tumor Necrosis Factor-a Antibody Adalimumab (D2E7) in Patients with Rheumatoid Arthritis," The Journal of Rheumatology, 29(11): 2288-2298 (2002).
Den Broeder et al., "Long term anti-tumour necrosis factor a monotherapy in rheumatoid arthritis: effect on radiological course and prognostic value of markers of cartilage turnover and endothelial activation," Ann. Rheum. Dis., 61:311-318 (2002).
Den Broeder et al., "The Effect of D2E7, a new human anti-TNFa monoclonal antibody, on the oxidative burst of PMN in patients with RA," Arthritis and Rheumatism, 41(9):S57 (1998).
Department of Surgery, University of Toronto, Annual Report (1998-1999) found online at http://www.surQ.med.utoronto.ca/AnnRep/AR98 99/index.html.
Dernis et al., "Infliximab in spondylarthropathy-Influence on bone density," Clin Exp Rheumatol, 20(6 Suppl 28):S185-6 (2002).
Deutsche Apothekerzeitung, 14:1574-1575 (2003).
DiSepio et al., "Novel approaches for the treatment of psoriasis," Drug Discovery Today, 4:222-231 (1999).
Doring et al., "Identification and Characterization of a TNFa Antagonist Derived From a Monoclonal Antibody," Mol. Immunol., 31:1059-1067 (1994).
Dubin et al., "Biologics for psoriasis," Nature Reviews, 2:855-856 (2003).
Eckelbecker, Lisa, "Cranking out doses," Worcester, Mass. Telegram & Gazette, p. E1 (Jan. 3, 2003).
Eckelbecker, Lisa, "D2E7 Placed Before FDA; Approval Sought for Local Drug," Worcester, Mass. Telegram & Gazette, p. E1 (Apr. 10, 2002).
Egan et al., "A randomized, single-blind, pharmacokinetic and dose response study of subcutaneous methotrexate, 15 and 25 MG/week, for refractory ulcerative colitis and Crohn's Disease," Gastroenterology, 114(4):G3978 (1998).
Eisermann et al., "Tumor necrosis factor in peritoneal fluid of women undergoing laparoscopic surgery," Fertility and Sterility, 50:573 (1988).
Elewski, "Infliximab for the treatment of severe pustular psoriasis," J. Am. Acad. Dermatol, 47(5):796-7 (2002).
Elkayam et al., "From wheels to feet: a dramatic response of severe chronic psoriatic arthritis to etanercept," Ann. Rheumatic Diseases, 59:839 (2000).
Elliott et al., "Suppression of fever and the acute-phase response in a patient with juvenile chronic arthritis treated with monoclonal antibody to tumour necrosis factor-alpha (cA2)," British Journal of Rheumatology, 36(5): 589-593 (1997).
Elliott et al., "Treatment of rheumatoid arthritis with chimeric monoclonal antibodies to tumor necrosis factor a," Arthritis & Rheumatism, 36(12):1681-90 (1993).

(56) References Cited

OTHER PUBLICATIONS

Emerald BioSystems Wizard I & II Instructions [online], Jan. 22, 2011 [retrieved Jan. 6, 2015]. Retrieved from Internet Archive wayback machine: <https://web.archive.org/web/20010122011100/http://www.emeraldbiostructures.com/wiz_instructions.htm>, 4 pages.

Emerald BioSystems Wizard II Formulations [online], Dec. 17, 2000 [retrieved Jan. 6, 2015]. Retrieved from Internet Archive wayback machine: <https://web.archive.org/web/20001217030900/http://www.emeraldbiostructures.com/wiz2_for mulations.htm>, 3 pages.

Emery et al., "Changes in PRO-MMP-1 in Relation to Standard Measures of Disease Activity Over a 6 Month Treatment Period with Adalimumab (D2E7) in Rheumatoid Arthritis," Arthritis & Rheumatism, 44(9):S215 (2001).

Emery et al., "Improvement in HAQ Disability in Rheumatoid Arthritis (RA) with Adalimumab (HUMIRA™) Based on Duration of Disease," Arthritis Rheum, 48(9):S313 (2003).

Enbrel (etanercept) Label, 2007.

Enbrel (etanercept) Physician Package Insert, Jun. 5, 2003.

ENBREL® (etanercept) Nov. 1998 Label.

Enhanced Online News, "Competition for early-line biologic use among psoriasis patients intensifies as Humira continues to gain ground on Enbrel," BusinessWire, Web, Oct. 5, 2011.

Ettehadi et al., "Elevated tumor necrosis factor-alpha (TNF-a) biological activity in psoriatic skin lesions," Clin. Exp. Immunol, 96:146-151 (1994).

Evaluate Group, "Abbott Laboratories' Investigational Fully Human Anti-TNF Therapy, D2E7 (Adalimumab), Shows Promise in Reducing the Signs and Symptoms of Rheumatoid Arthritis," Evaluate Group (Nov. 12, 2001) (http://www.evaluategroup.com/Universal/View.aspx?type=Story&id=14334) [accessed on Nov. 2, 2015].

EvaluatePharma press release, "Abbott Laboratories Announces Positive Results of Phase II Humira® (Adalimumab) Study in Psoriasis," archive of press release dated Feb. 9, 2004.

Examination Report in EP 07 150 442.7 mailed Oct. 18, 2011.

Fachinformation Humira® 40 mg/mL.

FDA approval of Humira (adalimumab): Prescribing information for Humira (adalimumab), Abbott Laboratories, North Chicago, IL, USA, Dec. 20, 2002, pp. 1-16.

FE Investigate, "ABT announces positive result," archive of Abbott Laboratories press release dated Feb. 9, 2004.

Feldmann et al., "Anti-TNFa Therapy of Rheumatoid Arthritis: What Have We Learned," Annu. Rev. Immunol., 19:163-196 (2001).

Figini et al., "In Vitro Assembly of Repertoires of Antibody Chains on the Surface of Phage by Renaturation," J. Mol. Biol., 239:68-78 (1994).

Finlay et al., "Dermatology Life Quality Index (DLQI)—a simple practical measure for routine clinical use," Clinical and Experimental Dermatology, 19:210-216, (1994).

Fleischmann et al., "Developing a new generation of TNF-alpha antagonists for the treatment of rheumatoid arthritis," Molecular Interventions, 3(6):310-318 (2003).

Flendrie et al., "Survival during treatment with tumor necrosis factor blocking agents in rheumatoid arthritis," Ann. Rheum. Dis., 62(2): ii30-ii33 (2003).

Fomsgaard et al., "Auto-antibodies to Tumour Necrosis Factor a in Healthy Humans and Patients with Inflammatory Diseases and Gram-Negative Bacterial Infections," Scand. J. Immunol, 30:219-23 (1989).

Foote et al., "Antibody Framework Residues Affecting the Conformation of the Hypervariable Loops," J. Mol. Biol., 224:487-499 (1992).

Foster et al., "Secondary glaucoma in patients with juvenile rheumatoid arthritis-associated iridocyclitis," Acta Opthalmol. Scand, 78(5):576-579 (2000).

Fox et al., "Sjogren's Syndrome," Arthritis and Rheumatism, 29:577-85 (1986).

Furst et al., "Updated consensus statement on biological agents, specifically tumour necrosis factor a (TNFa) blocking agents and interleukin-1 receptor antagonist (IL-1ra), for the treatment of rheumatic diseases," Ann Rheum Dis., 63(2): ii2-ii12 (2004).

Furst et al., "Adalimumab, a Fully Human Anti-Tumor Necrosis Factor-a Monoclonal Antibody, and Concomitant Standard Antirheumatic Therapy for the Treatment of Rheumatoid Arthritis: Results of STAR (Safety Trial of Adalimumab in Rheumatoid Arthritis)," The Journal of Rheumatology, 30(12):2563-2571 (2003).

Furst et al., "Improvement of the Individual ACR Components in ACR20 Responders in an Adalimumab (HUMIRA™) RA Clinical Trial," Arthritis Rheum, 48(9):S106 (2003).

Furst et al., "Safety and Efficacy of Adalimumab (D2E7), a Fully Human Anti-TNF-a Monoclonal Antibody, Given in Combination with Standard Antirheumatic Therapy: Safety Trial of Adalimumab in Rheumatoid Arthritis," Arthritis Rheum., 46(9):S572 (2002).

Furst et al., "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," Arthritis Rheum., 44(9):S215 (2001).

Genetic Engineering & Biotechnology News, "Top 20 Best-Selling Drugs of 2012," Mar. 5, 2013.

Genovese et al., "Adalimumab efficacy in patients with psoriatic arthritis who failed prior DMARD therapy," Ann Rheum Dis., 64(3):313 (2005).

Genovese et al., "Safety and efficacy of adalimumab in treatment of patients with psoriatic arthritis who had failed DMARD therapy," J Rheumatol, 34:1040-1050 (2007).

Genovese et al., "Treatment of Rheumatoid Arthritis with Etanercept," Rheum Dis Clin N Am., 30(2):311-28, vi-vii (2004).

Gerloni et al., "Infliximab in the treatment of persistently active refractory juvenile idiopathic (chronic) arthritis: A short-term pilot study," Arthritis & Rheumatism 43(9): S256, abstract #1139 (2000).

Giannini et al., "Preliminary definition of improvement in juvenile arthritis," Arthritis & Rheumatism, 40:1202 (1997).

Gibaldi, Biopharmaceutics and Clinical Pharmacokinetics, 4th ed. at 12-13 (1991).

Gibaldi, M. & Perrier, D., Pharmacokinetics, 2d ed. (1982).

Goldenberg, "Pharmaceutical-Approval Update," P&T 28(4):254-258 (2003).

Goldenberg, M.M., "Trastuzumab, a recombinant DNA-derived humanized monoclonal antibody, a novel agent for the treatment of metastatic breast cancer," Clinical Therapeutics, 21(2):309-318 (1999).

Gordon et al., "Adalimumab efficacy and safety in patients with moderate to severe chronic plaque psoriasis: preliminary findings from a 12-week dose-ranging trial," Poster presented Feb. 2004 at the American Academy of Dermatology Meeting, Journal of the American Academy of Dermatology. 50(3): P1 (2004).

Gordon et al., "Clinical Response to Adalimumab Treatment in Patients with Moderate to Severe psoriasis: Double-Blind, Randomized Controlled Trial and Open-Label Extension Study," J. Am. Acad. Derm., 55(1):598-606 (2006).

Gordon et al., "Definitions of measures of effect duration for psoriasis treatments," Archives of Dermatology, 141(1):82-84 (2005).

Gorman et al., "Treatment of ankylosing spondylitis by inhibition of tumor necrosis factor alpha," N Engl J Med., 346(18):1349-56 (2002).

Goto et al., "Adalimumab," Medline AC NLM12510366 (2002).

Goto et al., "Adalimumab," Nippon Rinsho (Japanese Journal of Clinical Medicine ), 60(12): 2384-2389 (2002).

Gottlieb et al., "The National Psoriasis Foundation Psoriasis Score System Versus the Psoriasis Area Severity Index and Physician's Global Assessment: A Comparison," Journal of Drugs in Dermatology, 3:260-266 (2003).

Gottlieb, "Efficacy of etanercept (Enbrel R) in patients with psoriasis," Abstract EULAR (2002).

Gottlieb, "Pharmacodynamic and pharmacokinetic response to anti-tumor necrosis factor-α monoclonal antibody (infliximab) treatment of moderate to severe psoriasis vulgaris," 48(1):68-75 (2003).

(56) References Cited

OTHER PUBLICATIONS

Gottlieb, A., "Infliximab for psoriasis," J. Am. Acad. Dermatol. 49(2):S112-117 (2003).
Gottlieb, A., et al., "Infliximab monotherapy provides rapid and sustained benefit for plaquetype psoriasis," J. Am. Acad. Dermatol., 48(6):829-835 (2003).
Granneman et al., "Pharmacokinetic/Pharmacodynamic (PKIPD) Relationships of Adalimumab (HUMIRA™, Abbott) in Rheumatoid Arthritis (RA) Patients during Phase II/III Clinical Trials," Arthritis. Rheum., 48(9):S140 (2003).
Griffiths et al., "Human anti-self antibodies with high specificity from phage display libraries," The EMBO J., 12(2):725-34 (1993).
Grom et al., "Patterns of Expression of Tumor Necrosis Factor a, Tumor Necrosis Factor a, and Their Receptors in Synovia of Patients with Juvenile Rheumatoid Arthritis and Juvenile Spondylarthropathy," Arthritis & Rheumatism, 39(10):1703-1710 (1996).
Guidance for Industry E6 Good Clinical Practice: Consolidated Guidance, The International Conference on Harmonisation of Technical Requirements for Registration of Pharmaceuticals for Human Use (ICH), (1996).
Halme, "Release of tumor necrosis factor-a by human peritoneal macrophages in vivo and in vitro," Am J Obstet Gynecol, 161:1718 (1989).
Harris et al., "Expression of proinflammatory Genes During Estrogen-Induced Inflammation of the Rat Prostate," Prostate, 44:19-25 (2000).
Hawkins et al., "Selection of Phage Antibodies by Binding Affinity Mimicking Affinity Maturation," J. Mol. Biol., 226:889-896 (1992).
HERCEPTIN® (trastuzumab) Label (Sep. 1998).
Highlights of HUMIRA Prescribing Information, Abbott Laboratories, North Chicago, IL, USA, pp. 1-53, updated Mar. 2009.
Highlights of HUMIRA Prescribing Information, Abbott Laboratories, North Chicago, IL, USA, pp. 1-70, updated Mar. 2011.
Hitt, E, "Adalimumab effective for psoriasis," Medscape, Feb. 10, 2004.
Holler et al., "Modulation of Acute Graft-Versus-Host Disease After Allogeneic Bone Marrow Transplantation by Tumor Necrosis Factor a (TNFa) Release in the Course of Pretransplant Conditioning: Role of Conditioning Regimens and Prophylactic Application of a Monoclonal Antibody Neutralizing Human TNFa (MAK 195F)," Blood, 86(3):890-899 (1995).
Holliger et al., "Engineered antibody fragments and the rise of single domains," Nature Biotechnology, 23(9): 1126-1136 (2005).
Holt et al., "Domain Antibodies: Proteins for Therapy," Trends in Biotech, 21(11): 484-490 (2003).
Honkanen et al., "Infliximab Treatment in the refractory chronic uveitis of juvenile idiopathic arthritis (JRA)," Arthritis & Rheumatism, 44:277-390, (2001) abstract #1438.
Hoogenboom et al., "Converting rodent into human antibodies by guided selection," Antibody Engineering, 8:169-185 (1996).
Horneff et al., "TNF-alpha antagonists for the treatment of juvenile-onset spondyloarthritides," Clin Exp Rheumatol, 20(6 Supp 28):S137-42 (2002).
Humira (Adalimumab) European Medicines Agency (EMA) Label (Sep. 12, 2008).
HUMIRA (adalimumab) Package Insert. Dec. 20, 2002. Retrieved from the Internet Dec. 11, 2009; <http://www.fda.gov/cder/foi/label/2002/adalabb1231 021b.pdf>; p. 1-3, 6.
HUMIRA (adalimumab) Patient Information Label (Dec. 2002).
HUMIRA (adalimumab). Data Sheet [online]. Abbott Laboratories, Dec. 20, 2002 [retrieved on Jun. 7, 2013]. Retrieved from the Internet: URL: www.fda.gov/downloads/Drugs/DevelopmentApprovalProcess/HowDrugsareDevelopedandAp proved/ApprovalApplications/TherapeuticBiologicApplications/ucm092762.pdf.
HUMIRA , Highlights of Prescribing Information, Abbott Laboratories, North Chicago, IL, USA, pp. 1-56, Nov. 2009.
Humira FDA approval letter for Adalimumab for the treatment of RA, Dec. 31, 2002.
Humira FDA approval letter for PsA, Oct. 3, 2005.
HUMIRA Prescribing Information, Abbott Laboratories, North Chicago, IL, USA, pp. 1-13, Jan. 2003.
HUMIRA Prescribing Information, Abbott Laboratories, North Chicago, IL, USA, pp. 1-33, Sep. 27, 2005.
HUMIRA Prescribing Information, Abbott Laboratories, North Chicago, IL, USA, pp. 1-24, Jul. 30, 2004.
HUMIRA product monograph (May 2013).
Huse et al., "Generation of a large combinatorial library of the immunoglobulin repertoire in phage lambda," Science, 246:1275-81 (1989).
Immunex Press Release, "First Therapy Approved for Treatment of psoriatic Arthritis," http://www.psoriasis-netz.de/medikamente/etanercept/pm-enbrel.html Jan. 2002.
Inpharma newsletter, "Adalimumab has achieved significant reductions in disease activity in patients with moderate-to-severe chronic plaque psoriasis," 1424(1): 6, Feb. 14, 2004.
International Preliminary Examination Report for PCT/US2003/022566 (WO 04/009776).
Iyer et al., "Etanercept for severe psoriasis and psoriatic arthritis: observations on combination therapy," Br. J. Dermatol, 146(1):118-21 (2002).
Jacobi et al., "Therapeutic application of TNF-alpha inhibitors infliximab and etanercept in inflammatory skin disorders," JDDG 1:259-272 (2003).
Janeway, "The protein products of MHC class I and class II genes are highly polymorphic," Immunobiology (3rd Edition) 4:24-4:30 (1997).
Janeway, "The structure of a typical antibody molecule," Immunobiology, 5 (2001).
Jespers et al., "Guiding the Selection of Human Antibodies from Phage Display Repertoires to a Single Epitope of an Antigen," Bio/Technology, 12:899-903 (1994).
Kaiser et al., "Efficacy of infliximab (Remicade) in the treatment of spondyloarthropathies two case reports," Joint Bone Spine, 68(6):525-7 (2001).
Kalden et al., "Emerging role of anti-tumor necrosis factor therapy in rheumatic diseases," Arthritis Research, 4(2): S34-40 (2002).
Kamarashev et al., "Generalised pustular psoriasis induced by cyclosporin a withdrawal responding to the tumour necrosis factor alpha inhibitor etanercept," Dermatology, 205(2):213-6 (2002).
Kameda et al., "Treatment of Chronic Inflammatory Diseases by Targeting TNF," Journal of Clinical and Experimental Medicine, 208(5):336-342 (2004).
Kanakoudi-Tsakalidou et al., "Influenza vaccination in children with chronic rheumatic diseases and long-term immunosuppressive therapy," Clinical and Experimental Rheumatology, 19:589-594 (2001).
Katsanos, et al., "Axillary hidradenitis suppurativa successfully treated with infliximab in a Crohn's disease patient," AJG 97:2155-2156 (2002).
Kavanaugh et al., "Adalimumab treatment with and without methotrexate in patients with moderate to severe psoriatic arthritis: results from ADEPT," Ann Rheum Dis., 64(3):325 [FRI0227] (2005).
Kavanaugh et al., "Immune Response is Not Affected by Adalimumab Therapy," Ann. Rheum. Dis., 62(1): 169 (2003).
Kavanaugh et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis," Ann. Rheum. Dis., 61(1):S168 (2002).
Kavanaugh et al., "Treatment with Adalimumab (D2E7) does not Affect Normal Immune Responsiveness," Arthritis Rheum., 46(9):S132 (2002).
Kaymakcalan et al., "Comparison of Adalimumab (D2E7), Infliximab, and Etanercept in the Prevention of Polyarthritis in the Transgenic Murine Model of Rheumatoid Arthritis," Arthritis Rheum., 46(9):S304 (2002).
Kaymakcalan et al., "Murine Model for Assessing Adalimumab, Inflixmab, and Etanercept to Prevent Polyarthritis," Ann. Rheum. Dis., 62(1):136-7 (2003).

(56) References Cited

OTHER PUBLICATIONS

Keffer et al., "Transgenic Mice 1 Expressing Human Tumour Necrosis Factor: A Predictive Genetic Model of Arthritis," EMBO (European Molecular Biology Organization) Journal, 10(13):4025-4031 (1991).
Kempeni, "Preliminary Results of early clinical trials with the fully human anti-TNFα monoclonal antibody D2E7," Ann. Rheum. Dis., 58(1):170-172 (1999).
Kempeni, "Update on D2E7: a fully human anti-tumour necrosis factor a monoclonal antibody," Ann. Rheum. Dis., 59(1):144-145 (2000).
Keystone et al, "Radiographic, clinical and functional outcomes with adalimumab (a human anti-TNF monoclonal antibody) in the treatment of patients with active rheumatoid arthritis on concomitant methotrexate therapy: A randomized, placebo-controlled, 52-week trial," Arthritis Rheum;50(5):1400-1411 (2004).
Keystone et al., "Adalimumab Inhibits the Progression of Structural Joint Damage in Patients with Active RA," Ann. Rheum. Dis., 62(1):64-65 (2003).
Keystone et al., "Efficacy and Safety of Adalimumab (D2E7), the Fully Human Anti-TNF Monoclonal Antibody, in MTX Partial Responders: Results of the 24-week ARMADA Trial," JCR: Journal of Clinical Rheumatology, 8(3):S69 (2002).
Keystone et al., "Subgroup Analysis of Radiographic Progression in RA Patients with Moderate Disease Treated with Adalimumab (HUMIRA®)," Ann. Rheum. Dis., 62(1):169 (2003).
Keystone et al., "Sustained Radiographic Inhibition with Adalimumab (HUMIRA®) over 2 years in Patients with Long Standing Rheumatoid Arthritis (RA)," Arthritis Rheum., 48(9):S315 (2003).
Keystone et al., "The Armada Trial: A Double-Blind Placebo Controlled Trial of the Fully Human Anti-TNF Monoclonal Antibody, Adalimumab (D2E7), in Patients with Active RA on Methotrexate (MTX)," Arthritis & Rheumatism, 44(9):S213 (2001).
Keystone et al., "The Fully Human Anti-TNF Monoclonal Antibody, Adalimumab (D2E7), Dose Ranging Study: The 24-Week Clinical Results in Patients with Active RA on Methotrexate Therapy (The ARMADA Trial)," (EULAR), Prague, Czech Republic, (2001).
Keystone, E., et al., "Radiographic Inhibition of Structural Damage Sustained in Patients with Long-standing Rheumatoid Arthritis Following 3 Years of Treatment with Adalimumab (HUMIRA®) Plus Methotrexate," Abstract 370, Arthritis & Rheumatism, 50 (Suppl. 9):S189 (2004).
Keystone, E., et al., "Subgroup Analysis of Radiographic Progression in RA Patients with Moderate Disease Treated With Adalimumab (Humira®)," Abstract FRI0064, Ann. Rheum. Dis., 63 (2004).
Keystone, et al., "Response to Adalimumab in Patients with Early Versus Late Rheumatoid Arthritis (RA)," Ann. Rheum. Dis., 62(1):170 (2003).
Kietz et al., "Clinical response to etanercept in polyarticular course juvenile rheumatoid arthritis," J. Rheumatology, 28(2):360-362 (2001).
Kimball et al., "Approved Adalimumab Dosing Regimen Associated With Greater Efficacy and Lower Cost per Responder Compared With 40-mg Every Other Week Dosing Without Initial 80-mg Dose: Analysis of Outcomes From Adalimumab Psoriasis Clinical Trial Database," 20th Congress of the Eur. Acad. Dermatol. Venereol. (Oct. 20-24, 2011) Lisbon, Portugal (FC01.8) (2013).
Kirby et al., "Successful treatment of severe recalcitrant psoriasis with combination infliximab and methotrexate," Clin. Exp. Dermatol, 26(1):27-9 (2001).
Klippel et al., "A. Epidemiology, Pathology, and Pathogenesis," Primer on Rheumatic Diseases, 11:155 (1997).
Klippel et al., "A. Juvenile Rheumatoid Arthritis and Juvenile Spondyloarthropathies," Primer on Rheumatic Diseases, 11:393 (1997).
Klippel, et al., "Juvenile Idiopathic Arthritis C. Treatment and Assessment," Primer on Rheumatic Diseases, 13:154-162 (2008).

Koo et al., "Update on the mechanisms and efficacy of biological therapies for psoriasis," Journal of Dermatological Science, 38(2):75-87 (2005).
Koski et al., "Tumor necrosis factor-alpha and receptors for it in labial salivary glands in Sjogren's syndrome," Clin Exp Rheumatol., 19:131 (2001).
Kraetsch et al., "Successful treatment of a small cohort of patients with adult onset of Still's disease with infliximab: first experiences," Annals of the Rheumatic Diseases, 60(3):iii55-iii57 (2001).
Krause, Carey, "Abbott bets on adalimumab in biologics RA market," Chemical Market Reporter, 261(25):12 (Jun. 24, 2002).
Kremer, "Rational Use of New and Existing Disease-Modifying Agents in Rheumatoid Arthritis," Ann. Intern. Med., 134:695-706 (2001).
Kress, Scheldon, "Clinical Review: Abbott, Biologic Licensing Application STN 125057, Adalimumab—For Use in the Treatment of Rheumatoid Arthritis," Center for Biologics Evaluation and Research, available at http://www.fda.gov/ohrms/dockets/ac/03/briefing/3930B1_01_C--Humira.Med.Review.pdf (2002).
Kurschat et al., "Treatment of psoriatic arthritis with etanercept," JAM Acad Dermatology, 44(6): 1052 (2001).
Kyle et al., "Guideline for anti-TNF-alpha therapy in psoriatic arthritis," Rheumatol., 44(3):390-7 (2005).
Landenne et al., "Infliximab or etanercept in the treatment of children with refractory juvenile idiopathic arthritis: an open label study," Ann. Rhem. Dis., 62(3):245-247 (2003).
Landenne et al., "Infliximab vs Etanercept in the treatment of severe juvenile chronic arthritis," Arthritis & Rheumatism, 43(1): S381 abstract #1888 (2001).
Langely et al., "Long-term safety and efficacy of adalimumab in the treatment of moderate to severe chronic plaque psoriasis," J of the Am Academy of Dermatology, 52(3):P8 (2005).
Langley et al., "Benefit-risk assessment of tumour necrosis factor antagonists in the treatment of psoriasis," Br. J. Dermatol., 162(6):1349-58 (2010).
Lerner et al., "Antibodies without immunization," Science, 258:1313-14 (1992).
Leusch et al., "Failure to demonstrate TNFa-specific autoantibodies in human sera by ELISA and Western blot," J. Immunol Methods, 139:145-47 (1991).
Lewis et al., "Use of alanine scanning mutagenesis to improve the affinity of an anti gp120 (HIV) antibody," J. Cell. Biochem., 18D:215 (1994).
Li et al., "The TNF-alpha transgenic mouse model of inflammatory arthritis," Springer Seminars in Immunopathology, 25(1):19-33 (2003).
Lipsky et al., "Infliximab and Methotrexate in the Treatment of Rheumatoid Arthritis," The New England Journal of Medicine, 343(22):1594-1602 (2000).
Lipsy, "Etanercept and its implications for managed care," Am J of Managed Care, 8(6):S194-S200 (2002).
Lorenz et al., "Perspectives for TNF-alpha-targeting therapies," Arthritis Research, 4(3):S17-S24 (2002).
Lorenz et al., "Technology evaluation: Adalimumab, Abbott Laboratories," Current Opinions in Molecular Therapeutics, 4(2): 185-190 (2002).
Low et al., "Mimicking Somatic Hypermutation: Affinity Maturation of Antibodies Displayed on Bacteriophage Using a Bacterial Mutator Strain," J. Mol. Biol., 260:359-368 (1996).
Low, thesis extract, Cambridge University (1996).
MacCallum et al., "Antibody-antigen Interactions: Contact Analysis and Binding Site Topography," J. Mol. Biol., 262:732-745 (1996).
MacDonald et al., "Tumor necrosis factor-alpha and interferon-gamma production measured at the single cell level in normal and inflamed human intestine," Clin. Exp. Immunol., 81:301-305 (1990).
Machold et al., "Adalimumab—a new TNF-a antibody for treatment of inflammatory joint disease," Expert Opin. Biol. Ther., 3(2):351-360 (2003).
Mackiewicz et al., "Dual effects caspase-1, interleukin-1beta, tumour necrosis factor-alpha and nerve growth factor receptor in inflammatory myopathies." Clin. Exp. Rheumatol, 21(1):41-8 (2003).

(56) References Cited

OTHER PUBLICATIONS

Mader et al., "Does injectable gold retard radiologic evidence of joint damage in psoriatic arthritis?" Clin. Invest. Med., 18(2):139-143 (1995) [abstract].
Maini et al., "How does infliximab work in rheumatoid arthritis?" Arthrit. Res, 4(2):S22-S28 (2002).
Maini et al., "Infliximab (chimeric anti-tumour necrosis factor a monoclonal antibody) versus placebo in rheumatoid arthritis patients receiving concomitant methotrexate: a randomised phase III trial," The Lancet, 354:1932-39 (1999).
Maksymowych et al., "Canadian Rheumatology Association Consensus on the use of anti-tumor necrosis factor-alpha directed therapies in the treatment of spondyloarthritis," J Rheumatol, 30(6):1356-63 (2003).
Maksymowych., "Update on the treatment of ankylosing spondylitis," Therapeutics and Clinical Risk Management, 3(6):1125-33 (2007).
Mang et al., "Response of severe psoriasis to infliximab," Dermatology, 204(2):156-7 (2002).
Mang et al., "TNF-alpha Antagonisten in der Therapie der Psoriasis Nutzen and Risiken," Z. Hautkr 77:548-550 (2002).
Mangge et al., "Serum cytokines in juvenile rheumatoid arthritis," Arthritis Rheum. 8:211 (1995).
Mangge et al., "Therapeutic experience with infliximab in a patient with polyarticular juvenile idiopathic arthritis and uveitis," Rheumatol Int., 5:258-261 (2003).
Marks et al., "By-Passing Immunization: Building High Affinity Human Antibodies by Chain Shuffling," Nature Biotechnology, 10:779-783 (1992).
Marks et al., "By-passing immunization: Human antibodies from V-gene libraries displayed on phage," J. Mol. Biol., 222:581-97 (1991).
Martinez et al., "Hidradenitis Suppurativa and Crohn's disease: Response to Treatment with Infliximab," Inflammatory Bowel Diseases, 7(4):323-326 (2001).
Marzella et al., "Briefing Document: Biologic License Application STN BL 125036/0 for alefacept for treatment of chronic plaque psoriasis," 1-111 (2002).
Marzi et al., "Effect of anti-tumor necrosis factor a on leukocyte adhesion in the liver after hemorrhagic shock: An intravital microscopic study in the rat," Shock, 3(1): 27-33 (1995).
Marzo-Ortega et al., "Infliximab is Effective in the Treatment of Resistant Psoriatic Arthritis and Skin Psoriasis: A Clinical and MRI Study," Rheumatology, 41(2):5 (2002).
Marzo-Ortega et al., "Inhibition of tumor necrosis factor alpha and ankylosing spondylitis," N Engl J Med., 348(4):359-61 (2003).
Massarotti et al., "Treatment Patterns in Early-onset Rheumatoid Arthritis (RA): Results from the Sonora Study," Ann. Rheum. Dis., 61(1):S93 (2002).
Mazumdar et al., "Golimumab," mAbs, 1:442-431 (2009).
McClure et al., "Comparative tolerability of systemic treatments for plaque-type psoriasis," Drug Safety, 25(13):913-27 (2002).
Mease et al., "Adalimumab for the treatment of patients with moderately to severely active psoriatic arthritis: results of a double-blind, randomized, placebo-controlled trial," Arthritis and Rheumatism, 52(10):3279-3289 (2005).
Mease et al., "Adalimumab therapy in patients with psoriatic arthritis: 24-week results of a phase III study," Arthritis & Rheumatism, 50(12):4097 (2004).
Mease et al., "Etanercept in the treatment of psoriatic arthritis and psoriasis: a randomised trial," Lancet, 356(9227):385-90 (2000).
Mease et al., "Etanercept Treatment of Psoriatic Arthritis," Arthritis & Rheumatism, 50(7):2264-2272 (2004).
Mease et al., "Psoriatic Arthritis Treatment: Biological Response Modifiers," Annals of the Rheumatic Diseases, 64(2):ii78-ii82 (2005).
Mease et al., "Quality-of-life issues in psoriasis and psoriatic arthritis: Outcome measures and therapies from a dermatological perspective", J. Amer. Acad. Dermatol. 54:685-704 (2006).
Mease, "Adalimumab: an anti-TNF agent for the treatment of psoriatic arthritis," Expert Opin. Biol. Ther., 5(11):1491-1504 (2005).
Mease, "Cytokine blockers in psoriatic arthritis," Ann Rheum Dis, 60:iii37-iii40 (2001).
Mease, "Etanercept: A new era in the treatment of psoriatic arthritis," Am J of Managed Care, 8(6):S181-S193 (2002).
Mease, "Tumour necrosis factor (TNF) in psoriatic arthritis: pathophysiology and treatment with TNF inhibitors," Ann Rheum Dis., 61:298-304 (2002).
Mease, J et al., "Application and modification of minimal disease activity measures for patients with Psoriatic Arthritis Treated with Adalimumab: subanalyses of ADEPT," J. Rheumatology, 40:647-652 (2013).
Mease, P., et al., "24-Week Efficacy and Safety Results From the Adalimumab Effectiveness in Psoriatic Arthritis Trial (ADEPT)," Rheumatology, 44:OP5 (2005).
Mease, P., et al., "Clinical Efficacy and Safety of Adalimumab for Psoriatic Arthritis: 48-Week Results of ADEPT," Abstract 500, Arthritis & Rheumatism, 52(9) (Suppl.):S215 (2005).
Mease, P., et al., "Enbrel® (Etanercept) in Patients with Psoriatic Arthritis and Psoriasis," Abstract 1835, Arthritis Rheum., 42 (suppl.):S377 (1999).
Mease, P., et al., "Inhibition of Joint Destruction in PsA with Adalimumab: 48-Week Results of ADEPT," Abstract 1699, Arthritis & Rheumatism, 52(9) (Suppl.):S631 (2005).
Medynski, "Phage Display: All Dressed Up and Ready to Role," Bio/Technology, 12:1134-1136 (1994).
Menter A, "Anti-TNF Therapies for Psoriasis," Japanese Journal of Clinical Immunology, 27(4):236 (2004).
Menter et al., "Adalimumab efficacy and safety results in patients with moderate to severe chronic plaque psoriasis with and without psoriatic arthritis," J Am Academy of Dermatology, 52(3):P174 (2005).
Mishra et al., "Histone deacetylase inhibitors modulate renal disease in the MRL-lpr/lpr mouse," J Clin Invest., 111(4):539-552 (2003).
Moller et al., "Monoclonal antibodies to human tumor necrosis factor a: in vitro and vivo application," Cytokine, 2(3):162-69 (1990).
Moretti et al., "New insights in the pathogenesis of vitiligo: Imbalance of epidermal cytokines at sites of lesions," Pigment Cell Res., 15(2):81-92 (2002).
Moretti et al., "Vitiligo and Epidermal Microenvironment: Possible Involvement of Keratinnocyte-Derived Cytokines," Arch. Dermatol, 138(2):273-4 (2002).
Mori et al., "Peritoneal fluid interleukin-1/b and tumor necrosis factor in patients with benign gynecologic disease," Am J Reprod Immunol, 26:62 (1991).
Mrowietz, "Definition of treatment goals for moderate to severe psoriasis: a European consensus," Arch. Dermatol. Res. 303(1):1-10 (2011).
Mullan et al., "Disease-modifying anti-rheumatic drug therapy and structural damage in early rheumatoid arthritis," Clinical and Experimental Rheumatology, 21(31):S158-164 (2003).
Murota et al., "Disruption of tumor necrosis receptor P55 impairs collagen turnover in experimentally induced sclerodermic skin fibroblasts," Arthritis Rheum, 48(4):1117-25 (2003).
Mussi et al., "Serum TNF-alpha levels correlate with disease severity and are reduced by effective therapy in plaque-type psoriasis," J Bil Reul Homeost Agents, 11(3):115-8 (1997).
Nadler et al., "11-1 Band TNF-a in prostatic secretions are indicators in the evaluation of men with chronic prostatitis," Journal Urology, 164:214 (2000).
Nash et al., "Psoriatic arthritis therapy: NSAIDS and traditional DMARDs," Ann Rheum Dis 64(2):ii74-ii77 (2005).
Neuner et al., "Cytokine release by peripheral blood mononuclear cells is affected by 8-methoxypsoralen plus UV-A," Photochem Photobiol., 59(2):182-188 (1994).
Newland et al., "Rapid response to infliximab in severe pustular psoriasis, von Zumbusch type." Int. J. Derma tol., 41(7):449-52 (2002).

(56) References Cited

OTHER PUBLICATIONS

News release, "Abbott Laboratories Initiates Clinical Trials to Explore Use of HUMIRA® (adalimumab) in Psoriasis and Psoriatic Arthritis," Mar. 3, 2003.
Nickoloff et al., "Cellular Localization of Interleukin-8 and Its Inducer, Tumor Necrosis Factor-alpha in Psoriasis," Am. J. Pathology 138(1):129-140 (1991).
Nilsson, "Antibody engineering," Current Opinion in Structural Biology, 5:450-456 (1995).
O'Quinn et al. "The effectiveness of tumor necrosis factor a antibody (infliximab) in treating recalcitrant psoriasis: A report of 2 cases," Arch. Dermatol., 138(5):644-8 (2002).
Ogilvie et al., "Treatment of psoriatic arthritis with antitumor necrosis factor-a antibody clears skin lesions of psoriasis resistant to treatment with methotrexate," British Journal of Dermatology, 144(3):587-589, (2001).
Oh et al., "The potential angiogenic role of macrophages in the formation of choroidal neovascular membranes," Invest Ophthalmol Visual Sci, 40:1891 (1999).
Oh et al., "Treatment with anti-tumor necrosis factor alpha (TNF-alpha) monoclonal antibody dramatically decreases the clinical activity of psoriasis lesions," Journal of the American Academy of Dermatology, 42(5 Pt 1):829-30 (2000).
Orhan et al., "Seminal plasma cytokine levels in the diagnosis of chronic pelvic pain syndrome," Int J Urol, 8:495 (2001).
Osbourn et al., "From rodent reagents to human therapeutics using antibody guided selection," Methods, 36:61-68 (2005).
Overton et al., "Peritoneal fluid cytokines and the relationship with endometrosis and pain," Hum Reprod, 11:380 (1996).
Ozaktay et al., "Dorsal root sensitivity to interleukin-1 beta, interleukin-6 and tumor necrosis factor in rats," Eur Spine Journal, 11:467 (2002).
Partsch et al., "Highly increased levels of tumor necrosis factor-alpha and other proinflammatory cytokines in psoriatic arthritis synovial fluid," J. Rheumatol., 24(3):518-23 (1997).
Partsch et al., "T cell derived cytokines derived in psoriatic arthritis synovial fluids," Annals Rheumatoid Disease, 57:691 (1998).
Patel et al., "Adalimumab: efficacy and safety in psoriasis and rheumatoid arthritis," Dermatologic Therapy, 17(5):427-431 (2004).
Patentee's Submission in EP07150442.7 to the EPO dated Apr. 15, 2013.
Patentee's Submission in EP07150442.7 to the EPO dated Apr. 30, 2012.
Patentee's Submission in EP07150442.7 to the EPO dated Jun. 30, 2011.
Paul et al., "Assessment of patients with spondyloarthropathies for treatment with tumour necrosis factor alpha blockade," Rheumatol, 44:17-23 (2005).
Paul, "Immunogenicity and Antigen Structure," Fundamental Immunology, 3(242):292-295 (1993).
Paulus et al., "Relative contributions of the components of the American College of Rheumatology 20% criteria for improvement to responder status in patients with early seropositive rheumatoid arthritis," Arthritis & Rheumatism; 43(12): 2743-2750 (2000).
Peterson, "American College of Rheumatology New Orleans Oct. 25-29, 2002," Trends-in-Medicine, 1-12 (2002).
Pham et al., "Initiation of biological agents in patients with ankylosing spondylitis: results of a Delphi study by the ASAS Group," Ann Rheum Dis., 62(9):812-6 (2003).
Physician's Desk Reference, "Trexall," 57:833-836 (2003).
Pincus et al., "Combination Therapy with Multiple Disease-Modifying Antirheumatic Drugs in Rheumatoid Arthritis: A Preventive Strategy," Ann. Intern. Med., 131:768-774 (1999).
Pincus, T., et al., "Evidence from clinical trials and long-term observational studies that disease-modifying anti-rheumatic drugs slow radiographic progression in rheumatoid arthritis: updating a 1983 review," Rheumatology, 41:1346-1356 (2002).
PR Newswire, "Abbott Laboratories Announces Positive Results of Phase II HUMIRA® (adalimumab) Study in Psoriasis" (Feb. 9, 2004).
PR Newswire, "Abbott Laboratories' D2E7—the next generation anti-TNF—shows promise in rheumatoid arthritis patients," PR Newswire (Jun. 15, 2001) (http://www.prnewswire.co.uk/news-releases/abbott-laboratories-d2e7---the-next-generation-anti-tnf-shows-promise-in-rheumatoid%ADarthritis-patients-154493225.html) [accessed on Nov. 4, 2015].
PR Newswire, "Cambridge Antibody Technology Interim Results for the Six Months Ended Mar. 31, 2002" (May 20, 2002).
PR Newswire, "First Phase III data for Abbott Laboratories' D2E7 (Adalimumab) support promise in rheumatoid arthritis (RA)," PR Newswire (Jun. 14, 2002) (http://www.prnewswire.co.uk/news-releases/first-phase-iii-data-for-abbott-laboratories-d2e7-adalimumab-support-promise-in-rheumatoid-arthritis-ra-154758845.html) [accessed on Nov. 2, 2015].
Product Monograph for Humira adalimumab (#00148) CAS Registry No. 331731-18-1, Abbott Laboratories, Jul. 10, 2012: 1-93.
Proudfoot, S. & Collett, J., "Dosage regimens" in Pharmaceutics: The Science of Dosage Form Design, 2d ed. (Aulton, M.E., ed.), Chapter 19 at 275-288 (2001).
Pucino, Jr. et al., "Use of biologics in rheumatoid arthritis: Where are we going?" Am. J. Health-Syst. Phann., 63(18 Suppl 4):S19-41 (2006).
Queen et al., "A humanized antibody that binds to the interleukin 2 receptor," Proc. Natl. Acad. Sci. USA, 86:10029-10033 (1989).
Queiro-Silva et al., "A polyarticular onset predicts erosive and deforming disease in psoriatic arthritis," Ann. Rheum. Dis., 62:68-70 (2003).
R&D Focus Drug News, "Adalimumab Cambridge Antibody Technology clinical data" (Jul. 2, 2001) ("R&D Focus (2001)").
Rader et al., "A phage display approach to rapid antibody humanization: Designed combinatorial V gene libraries," Proc Natl. Acad Sci USA, 95:8910-8915 (1998).
Rau et al., "2.5-Year Treatment Results with Adalimumab (D2E7), the First Fully Human Anti-TNF Monoclonal Antibody, in Combination with Methotrexate in Active Rheumatoid Arthritis," Ann. Rheum. Dis., 61(1):S55 (2002).
Rau et al., "Adalimumab Inhibits Radiographic Disease Progression in Long-Standing, Rapidly Progressive Rheumatoid Arthritis," Ann. Rheum. Dis., 62(1):191 (2003).
Rau et al., "Combination therapy with the human anti-TNF antibody D2E7 and methotrexate in active chronic polyarthritis," Z. Rheumatol., 58(1): 1/35, F20 (1999).
Rau et al., "Effect and compatibility of repeated intravenous doses of the human anti-TNF antibody D2E7 in patients with chronic polyarthritis," Z. Rheumatol., 58(1):1/41, P12 (1999).
Rau et al., "Erfahrungen mit D2E7," Akt. Rheumatol., 25:83-88 (2000).
Rau et al., "Long-term efficacy and tolerability of multiple I.V. doses of the fully human Anti-TNF-Antibody D2E7 in patients with Rheumatoid Arthritis," Arthritis & Rheumatism, 41(137):S55 (1998).
Rau et al., "Long-term Treatment with the Fully Human Anti-TNF-Antibody D2E7 Slows Radio-graphic Disease Progression in Rheumatoid Arthritis," Arthritis and Rheumatism, 42(9):S400 (1999).
Rau et al., "Low dose prednilsolone therapy (LDPT) retards radiographically detectable destruction in early rheumatoid arthritis—Preliminary results of a multicenter, randomized, parallel, double blind study," Z. Rheumatol., 59(2):II/90-II/96 (2000).
Rau et al., "Treatment with Adalimumab (D2E7), the Fully Human Anti-TNF Monoclonal Antibody, Slows Radiographic Disease Progression in Rheumatoid Arthritis: Results of a 12-Month Study," J. Clin. Rheum., 8:S78 (2002).
Rau, "Adalimumab (a fully human anti-tumour necrosis factor a monoclonal antibody) in the treatment of active rheumatoid arthritis: the initial results of five trials," Ann. Rheum. Dis., 61(2):ii70-ii73 (2002).
Rau, "Experiments with D2E7," Z. Rheumatol., 58(1):1-21, S51 (1999).

(56) References Cited

OTHER PUBLICATIONS

Reilly et al., "Use of genetic knockouts to modulate disease expression in a murine model of lupus, MRUipr mice," Immunologic Research, 25(2):143-153 (2002).
Reimold, "New indications for treatment of chronic inflammation by TNF-alpha blockade," Am J Med Sci., 325(2):75-92 (2003).
Reimold, "TNF alpha as therapeutic target: New drugs, more applications," Current Drug Targets—Inflammation and Allergy, 1:377-392 (2002).
Reinhart et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care. Med., 24(5):733-742 (1996).
Remicade (Infliximab) Drug Information: Uses, Side Effects, Drug Interactions and Warnings http://www.rxlist.com/remicadedrug.htm.
Remicade (infliximab) product information Feb. 1, 2002, retrieved from http://www.drugbank.ca/system/fda_labels/DB00065.pdf?1265922797.
Remicade (infliximab) Product Label (Jun. 2002).
REMICADE™ (infliximab) Aug. 1998 Label.
REMICADE™ (infliximab) Nov. 10, 1999 Approval Letter.
Results of adalimumab phase II clinical trial M02-529.
Reuss-Borst et al., "Sweet's syndrome associated with myelodysplasia: possible role of cytokines in the pathogenesis of the disease," Br. J. Haematol., 84(2):356-8 (1993).
Revenga, F., et al., "Treatment of recalcitrant psoriasis with infliximab," Actas Dermo-Sifiliograficas, 95.1:44-50 (2004).
Revicki et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," Arthritis Rheum., 46(9):S537 (2002).
Ricardo, "Clinical benefits in patients with psoriasis after Efalizumab therapy: Clinical trial versus practice," Cutis 74:193-200 (2004).
Riechmann et al., "Phage Display and Selection of a Site-Directed Randomized Single-Chain Antibody Fv Fragment for Its Affinity Improvement," Biochemistry, 32:8848-8855 (1993).
Rinehart-Kim et al., "Alterations in the Gene Expression Profile of MCF-7 Breast Tumor Cells in Response to c-Jun," Int. J. Cancer, 88:180-190 (2000).
Ritchlin et al., "Patterns of cytokine productions in psoriatic synovium," J. Rheumatol, 25:1544 (1998).
Roberts et al., "Tumour necrosis factor inhibitors: risks and benefits in patients with rheumatoid arthritis," Int. Med. J., 34:687-693 (2004).
Rosenberg, Daniel, "Abbott sees new uses for rheumatoid arthritis drug [D2E7]," FirstWord Pharma (Sep. 9, 2002).
Rowland, M. & Tozer, T., Clinical Pharmacokinetics: Concepts and Applications, 3d ed.,; (1995).
Rudikoff et al., "Single amino acid substitution altering antigen-binding specificity," Proc. Natl. Acad. Sci. USA, 79(6):1979-1983 (1982).
Ruperto, "48-Week Data From the Study of Adalimumab in Children With Juvenile Rheumatoid Arthritis (JRA)," Ann. Rheum. Dis., 65(2):56 (2006).
Russell-Jones et al., "High-dose interferon and the U.K. guidelines for cutaneous melanoma," Br. J. Dermatol.,147(4):832-4 (2002).
Saini et al., "Advances in therapy for psoriasis: an overview of infliximab, etanercept, efalizumab, alefacept, adalimumab, tazarotene, and pimecrolimus," Current Pharmaceutical Design, 11(2):273-280 (2005).
Salfeld et al., "Generation of Fully Human Anti-TNF Antibody D2E7," Arthritis Rheum., 41(9):S57 (1998).
Sandborn et al., "An engineered human antibody to TNF (CDP571) for active Crohn's disease: a randomized double-blind placebo-controlled trial," Gastroenterology, 120:1330-1338 (2001).
Sandborn et al., "CDP571, a humanised monoclonal antibody to tumour necrosis factor α, for moderate to severe Crohn's disease: a randomized, double blind, placebo controlled trial," Gut, 53:1485-1491 (2004).
Sandborn et al., "Etanercept for Active Crohn's Disease: A Randomized, Double-blind, Placebo-Controlled Trial," Gastroenterol, 121:1088-1094 (2001).
Sandborn et al., "Infliximab in the Treatment of Crohn's Disease: A User's Guide for Clinicians," The American Journal of Gastroenterology, 97(12):2962-2972 (2002).
Sandborn, "Antitumor necrosis factor for inflammatory bowel disease: A Review of agents, pharmacology, clinical results, and safety," Inflamm. Bowel Disease, 5(2):199-233 (1999).
Santora et al., "Characterization of Noncovalent Complexes of Recombinant Human Monoclonal Antibody and Antigen Using Carbon Exchange, Size Exclusion Chromatography,and BIAcore," Analytical Biochemistry, 299(2):119-129 (2001).
Santora et al., "Characterization of Recombinant Human Monoclonal Tissue Necrosis Factor-a Antibody Using Cation-Exchange HPLC and Capillary Isoelectric Focusing," Analytical Biochemistry, 275:98-108 (1999).
Schattenkirchner et al, "Efficacy and Tolerability of Weekly Subcutaneous Injections of the Fully Human Anti-TNF-Antibody D2E7 in Patients with Rheumatoid Arthritis—Results of a Phase I Study," Arthritis and Rheumatism, 41(9):S57 (1998).
Schattenkirchner et al., "Long-term Use of the Fully Human Anti-TNF Antibody Adalimumab (D2E7) in Dmard-refractory Rheumatoid Arthritis," EULAR, Prague, Czech Republic, Jun. 2001.
Schattenkirchner et al., "Long-term Use of the Fully Human Anti-TNF Antibody D2E7 in Combination with Methotrexate in Active Rheumatoid Arthritis," EULAR 43(9) (suppl.) S228 (2000).
Schattenkirchner et al., "Phase 1 study on the effectiveness and compatibility of weekly subcutaneous injections of the human anti-TNF antibody D2E7 in chronic polyarthritis," Z.Rheumatol., 58(1):1-42, P14 (1999).
Scheinfeld, "Adalimumab (HUMIRA): A Review," J. Drugs Dermatol, 2:375-377 (2003).
Schiff et al., "A Randomized, Controlled, Safety Trial of Adalimumab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," Ann. Rheum. Dis., 61(1):S169 (2002).
Schiff et al., "Efficacy of Adalimumab Measured by the Disease Activity Score 28 (DAS28) and EULAR Response Criteria," Ann. Rheum. Dis., 62(1):170 (2003).
Schiff et al., "Malignancies in Rheumatoid Arthritis (RA) Clinical Trials with Adalimumab (HUMIRA)," Arthritis Rheum., 48(9):S700 (2003).
Schiff et al., "Rates of Infection in Adalimumab Rheumatoid Arthritis Clinical Trials," Ann. Rheum. Dis., 62(1):184 (2003).
Schiff et al., "Sustained Efficacy of Adalimumab (HUMIRA™) Plus Methotrexate in Rheumatoid Arthritis (RA) Patients," Arthritis Rheum., 48(9):S314 (Poster 740) (2003).
Schnarr et al., "Anti-tumour necrosis factor (TNF)-alpha therapy in undifferentiated spondyloarthropathy," Clin Exp Rheumatol, 20(6 Supp 28):S126-9 (2002).
Schneider, D., et al, "Safety, pharmacokinetics and biological activity of enlimomab (anti-ICAM-1 antibody): an open-label, dose escalation study in patients hospitalized for acute stroke," European Neurology, 40:78-83 (1998).
Schopf et al., "Treatment of psoriasis with the chimeric monoclonal antibody against tumor necrosis factor a, infliximab," J. Am. Acad. Dermatol, 46(6):886-91 (2002).
Shealy et al., "Anti-TNF-alpha antibody allows healing of joint damage in polyarthritic transgenic mice," Arthritis Research, Current Science, 4(5):R7 (2002).
Shealy et al., "Characterization of golimumab, a human monoclonal antibody specific for human tumor necrosis factor alpha," mAbs, 2(4):1-12 (2010).
Shikiar et al., "The validity and responsiveness of three quality of life measures in the assessment of psoriasis patients: results of a phase II study," Health and Quality of Life Outcomes 4:71 (2006).

(56) References Cited

OTHER PUBLICATIONS

Shikiar et al., "Validity and reliability of patient reported outcomes used in Psoriasis: results from two randomized clinical trials," Health and Quality of Life Outcomes, 1:53 (2003).
Shvidel et al., "Cytokine release by activated T-cells in large granular lymphocytic leukemia associated with autoimmune disorders," Hematol J., 3:32 (2002).
Sibilia, "Combination therapy for rheumatoid arthritis," Ann. Med. Interne., 153(1):41-52 (2002).
Siegel et al., "Evidence of Effects of a TNF Blocking Agent in ACR20 Non-Responders," Arthritis Rheum., 48(9):S127 (2003).
Sieper et al., "New treatment options in ankylosing spondylitis: a role for anti-TNFalpha therapy," Ann Rheum Dis., 60(3):iii58-61 (2001).
Sieper, J. & Braun, J., "Anti-TNF agents for the treatment of spondyloarthropathies," Expert Opinion on Emerging Drugs, 7(2):235-246 (2002) ("Sieper (2002)").
Silicon Investor blog, "Abbott Laboratories announces positive results of Phase II Humira® (adalimumab) study in psoriasis," reproduction of Abbott Laboratories press release at entry 457 of 625, dated Feb. 9, 2004.
Simon et al., "Studies on efficacy in psoriasis and psoriatic arthritis initiated," Dermatol. Psychosom., 4:100-102 (2003).
Sladden et al., "Extensive plaque psoriasis successfully treated with adalimumab (Humira)," The British Journal of Dermatology, 152(5):1091-1092 (2005).
Slatko, "Contender to the crown," MedAdNews, 29(7):1-3 (2010).
Smith et al., "British Association of Dermatologists guidelines for use of biological interventions in psoriasis 2005," Brit J. Dermatology., 153:486-497 (2005).
Smith, "Ibuprofen in psoriatic arthritis," Arthritis Rheum., 23(8):961-962 (1980).
Smolen et al., "A Comparison of the SDAI and DAS28 as Measures of Response in Adalimumab (HUMIRA™) Clinical Trials in Rheumatoid Arthritis (RA)," Arthritis Rheum., 48(9):S107 (2003).
Smolen et al., "Objectives and Strategies for Rheumatoid Arthritis Therapy: Yesterday vs. Today," Drugs of Today, 39(B):3-8 (2003).
Spencer-Green, "Etanercept (Enbrel): update on therapeutic use," Ann Rheum Dis., 59(1):i46-i49 (2000).
St. Clair, "Infliximab treatment for rheumatic disease: clinical and radiological efficacy," Ann Rheum Dis, 61(2):ii67-ii69 (2002).
Stockinger, "CD147," http://mpr.nci.nhi.gov (1999).
Stokes et al., "Potential of tumor necrosis factor neutralization strategies in Rheumatologic disorders other than rheumatoid arthritis," Semin Arthritis Rheum., 33(1):1-18 (2003).
Stone et al., "Clinical and imaging correlates of response to treatment with infliximab in patients with ankylosing spondylitis," J Rheumatol., 28(7):1605-14 (2001).
Strand et al., "Adalimumab Improves Health-related Quality of Life in Rheumatoid Arthritis Patients," Ann. Rheum. Dis., 62(1):356 (2003).
Strand et al., "Improvement in Health-related Quality of Life, Health Utility, and Fatigue in Patients with Active Rheumatoid Arthritis (RA) on Adalimumab (HUMIRA™, Abbott) Therapy," Arthritis Rheum., 48(9):S402 (2003).
Strand et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," Ann. Rheum. Dis., 61(1):S175 (2002).
Studnicka-Benke et al., "Tumor necrosis factor alpha and its soluble receptors parallel clinical disease and autoimmune activity in systemic lupus erythematosus," Br J Rheumatol., 35:1067 (1996).
Sun et al., "Bowel necrosis induced by tumor necrosis factor in rats is mediated by platelet-activating factor," J. Clin. Invest., 81:1328-1331 (1988).
Sun et al., "Individually Distinct Ig Homology Domains in PECAM-1 Regulate Homophilic Binding and Modulate Receptor Affinity," J. Biol. Chem., 271:11090-11098 (1996).

Takahashi, "Current Situation and Future View of Antibody Therapy for Inflammatory Diseases," Journal of Clinical and Experimental Medicine, 211(7):99746-751 (2004).
Takematsu, "Absence of tumor necrosis factor-alpha in suction blister fluids and stratum corneum from patients with psoriasis," Arch Dermatol Res., 281(6):398-400 (1989).
Taketani et al., "Comparison of cytokine levels and embryo toxicity in peritoneal fluid in infertile women with untreated or treated endometrosis," Am J Obstet. Gynecol., 167:265 (1992).
Taylor, "Anti-tumor necrosis factor therapies," Current Opinion in Rheumatology, 13:164-169 (2001).
Third Party Observations against EP07150442.7, filed Oct. 29, 2014.
Thomas, Taber's Cyclopedic Medical Dictionary, 13:118-119 (1977).
Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol., 256:77-88 (1996).
Thomson, "Abbott seeks U.S. and E.U. approval for D2E7 in rheumatoid arthritis," Reuters Drug News, Apr. 10, 2002, Retrieved from https ://integrity.thomsonpharma.com/integrity/xmlxs1/pk_ref_list.xml_show_ficha_ref?p_ref id=662437.
Thorp, "Tumour necrosis factor induction of ELAM-1 and ICAM-1 on human umbilical vein endothelial cells—analysis of tumour necrosis factor-receptor interactions," Cytokine, 4(4):313 (1992).
Tomlinson et al., "The Repertoire of Human Germline VH Sequences Reveals about Fifty Groups of VH Segments with Different Hypervariable Loops," J. Mol. Biol., 227:776-798 (1992).
Tomlinson et al., "The structural repertoire of the human VK domain," The EMBO Journal, 14(18):4628-4638 (1995).
Tracey et al., "Shock and tissue injury induced by recombinant human cachectin," Science, 234:470-474 (1986).
Tracey et al., "Tumor Necrosis Factor: A Pleiotropic Cytokine and Therapeutic Target," Annu. Rev. Med., 45:491-503 (1994).
Tsutsumimoto et al., "TNF-a and IL-1 B Suppress N-Cadherin Expression in MC3T3-E1 Cells," J Bone Miner Res., 14:1751 (1999).
Tugwell et al., "Adalimumab Improves Utility and Quality-adjusted Life Days in Rheumatoid Arthritis," Ann. Rheum. Dis., 62(1):107-8 (2003).
Tugwell et al., "Relationship Between ACR Response and HRQL in Adalimumab Clinical Trials," Ann. Rheum. Dis., 62(1):536 (2003).
Tutuncu et al., "Anti-TNF therapy for other inflammatory conditions," Clin. Exp. Rheumatol., 20(6Suppl28):S146-51 (2002).
Tyring et al., "Efficacy and Safety of HUMIRA Every-Other-Week Dosing: Pooled Clinical Trial Experience," Abstract, Presented at the 21st World Congress of Dermatology, Buenos Aires, Argentina, Sep. 30-Oct. 5, 2007.
Ueda et al., "Two Mouse Monoclonal Antibodies Detecting Two Different Epitopes of an Activated Lymphocyte Antigen on Adult T-Cell Leukemia Cells," Cancer Res. 45:1314-1319 (1985).
Vajdos et al., "Comprehensive Functional Maps of the Antigen-binding Site of an Anti-ErbB2 Antibody Obtained with Shotgun Scanning Mutagenesis," J. Mol. Biol., 320:415-428 (2002).
Van Assche, "Anti-TNF agents in Crohn's Disease," Expert Opin. Investig. Drugs., 9(1):103-11 (2000).
Van de Putte et al., "Adalimumab (D2E7) Monotherapy in the Treatment of Patients with Severely Active Rheumatoid Arthritis (RA)," Arthritis Rheum., 46(9):S171 (2002).
Van de Putte et al., "A placebo-controlled phase 1 study of the human anti-TNP-antibody D2E7 in patients with active chronic polyarthritis," Z. Rheumatol., 58(1):1-34, F19 (1999).
Van de Putte et al., "A Single Dose Placebo Controlled Phase I Study of the Fully Human Anti-TNF Antibody D2E7 in Patients with Rheumatoid Arthritis," Arthritis Rheum., 41:S57 (1998).
Van De Putte et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," JCR, 8(3):S89 (2002).

(56) References Cited

OTHER PUBLICATIONS

Van de Putte et al., "Adalimumab," TNFa-Inhibition in the Treatment of Rheumatoid Arthritis, 71-93 (2003).
Van de Putte et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," Ann. Rheum. Dis., 61(1):S168 (2002).
Van de Putte et al., "Efficacy and safety of adalimumab as monotherapy in patients with rheumatoid arthritis for whom previous disease modifying antirheumatic drug treatment has failed," Ann. Rheum Dis., 63:508-516 (2004).
Van de Putte et al., "Efficacy and safety of the fully human anti-tumour necrosis factor a monoclonal antibody adalimumab (D2E7) in DMARD refractory patients with rheumatoid arthritis: a 12 week, phase II study," Ann. Rheum. Dis., 62:1168-1177 (2003).
Van de Putte et al., "Efficacy of the Fully Human anti-TNF Antibody D2E7 in Rheumatoid Arthritis," Arthritis & Rheumatism, 42(1977):S400 (1999).
Van de Putte et al., "One Year Efficacy Results of the Fully Human Anti-TNF Antibody D2E7 in Rheumatoid Arthritis," Arthritis Rheum., 43(9):S269 (2000).
Van de Putte et al., "Sustained 5-Year Efficacy of Adalimumab (HUMIRA) Monotherapy in DMARD-Refractory rheumatoid arthritis (RA)," Arthritis Rheum., 48(9):S314 (2003).
Van den Bosch et al., "Crohn's disease associated with spondyloarthropathy: effect of TNF-alpha blockade with infliximab on articular symptoms," Lancet. 356(9244):1821-2 (2000).
Van den Bosch et al., "Effects of a loading dose regimen of three infusions of chimeric monoclonal antibody to tumour necrosis factor a (infliximab) in spondyloarthropathy: an open pilot study," Annal. Rheum. Dis. 59:428-433 (2000).
Van der Heijde, D., et al., "Psoriatic arthritis imaging: a review of scoring methods," Ann. Rheum. Dis., 64 (Suppl. II):ii61-ii64 (2005).
Van der Poll et al., "Effect of postponed treatment with an anti-tumour necrosis factor (TNF) F(ab')2 fragment on endotoxin-induced cytokine and neutrophil responses in chimpanzees," Clin. Exp. Immunol., 100:21-25 (1995).
Van Riel et al., "Long-Term Treatment with Adalimumab (D2E7) Using Background Methotrexate in Active Rheumatoid Arthritis: Results of a 3 Year Study," Arthritis Rheum., 46(9):S534 (2002).
Van Riel, "A Comparison of CRP and ESR to Measure the DAS28 in Adalimumab Clinical Trials," Ann Rheum Dis., 62:169-70 (Poster THU0199). (2003).
Vasilli, "The pathophysiology of tumor necrosis factors", Annu. Rev. Immunol., 10:411-452 (1992).
Vaughan et al., "Human antibodies by design," Nature Biotechnology, 16:535-539 (1998).
Velagapudi et al., "Pharmacokinetics of Adalimumab (D2E7), a Fully Human Anti-TNF-a Monoclonal Antibody, Following a Single Intravenous Injection in Rheumatoid Arthritis Patient Treated with Methotrexate," Arthritis Rheum., 46(9):S133 (2002).
Velagapudi, et al., "Effect of Methotrexate (MTX) Coadministration on the Pharmacokinetics (PK) of Adalimumab (HUMIRA™, Abbott) Following a Single Intravenous (iv) Injection," Arthritis Rheum., 48(9):S141 (2003).
Venn et al., "Elevated synovial fluid levels of interleukin-6 and tumor necrosis factor associated with early experimental canine osteoarthritis," Arthritis Rheum., 36:819-826 (1993).
Victor et al., "TNF-alpha and apoptosis: implications for the pathogenesis and treatment of psoriasis," J Drugs Dermatol, 1(3):264-75 (2002).
Vitali et al., "Preliminary criteria for the classification of sjogren's syndrome," Arthritis Rheum, 36:3407 (1993).
Wailoo et al., "Modeling the cost effectiveness of etanercept, adalimumab and anakinra compared to infliximab in the treatment of patients with rheumatoid arthritis in the medicare program," Agency for Healthcare Research and Quality, 1-74 (2006).

Wakefield et al., "The role of cytokines in the pathogenesis of inflammatory eye disease," Cytokine, 4:1 (1992).
Ward et al., "Binding activities of a repertoire of single immunoglobulin variable domains secreted from *Escherichia coli*," Nature, 341:544-546 (1989).
Website http://www.mayoclinic.com/health/psoriatic-arthritis/DS004 76, accessed Jan. 4, 2012.
Weinblatt et al., "Adalimumab, a Fully Human Anti-Tumor Necrosis Factor a Monoclonal Antibody, for the Treatment of Rheumatoid Arthritis in Patients Taking Concomitant Methotrexate," Arthritis & Rheumatism, 48(1):35-45 (2003).
Weinblatt et al., "The ARMADA Trial: Efficacy and Safety of Adalimumab in Patients with Active RA at 24 Months," Ann. Rheum. Dis., 62(1):98 (2003).
Weinblatt et al., "The ARMADA Trial: Sustained Efficacy After Dose Reduction of Concomitant Methotrexate and/or Corticosteroids in Patients With Rheumatoid Arthritis Treated With Adalimumab (HUMIRA®)," 2005 EULAR Annual Meeting, Jun. 8-11, 2005, Vienna, Austria (Poster SAT0083).
Weinblatt et al., "The Armada Trial: Sustained Improvement and Tolerability in Long-Term Follow-Up of Patients Treated with Adalimumab (HUMIRA™)," Arthritis Rheum., 48(9):S314 (2003).
Weinstein et al., Therapy of Moderate-to-Severe Psoriasis 2nd Ed, pp. 1-21 (2003).
Weisman et al., "A Dose Escalation Study Designed to Demonstrate the Safety, Tolerability and Efficacy of the Fully Human Anti-TNF Antibody, D2E7, Given in Combination with Methotrexate," Arthritis Rheum., 43(9):S391 (2000).
Weisman et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," Clinical Therapeutics, 25(6):1700-1721 (2003).
Weisman et al., The Importance of Pain and the Impact of Adalimumab on Pain in RA Patients, Ann. Rheum. Dis., 62(1):351 (2003).
Wellborne et al., "Adalimumab (D2E7), a Fully Human Anti-TNF-a Monoclonal Antibody, Improved Health-Related Quality of Life in Patients with Active Rheumatoid Arthritis Despite Concomitant Methotrexate Therapy," Arthritis Rheum., 46(9):S518 (2002).
Wells et al., "Incidence of Injection-Site Reactions Associated with Adalimumab (D2E7) Give Subcutaneously for at Least 6 Months: A Retrospective Analysis of 4 Phase II/III Clinical Trials," Arthritis Rheum., 46(9):S171 (2002).
Wells et al., "Injection-site Reactions in Adalimumab Rheumatoid Arthritis (RA) Pivotal Clinical Trials," Ann. Rheum. Dis., 62(1):411 (2003).
Westacott et al., "Tumor necrosis factor-a receptor expression on chondrocytes isolated from human articular cartilage," J. Rheumatology, 21:1710 (1994).
Wiendl et al., "Therapeutic Approaches in Multiple Sclerosis, Lessons from Failed and Interrupted Treatment Trials," Biodrugs, 16(3):183-200 (2002).
Williams et al., "Anti-tumor necrosis factor ameliorates joint disease in murine collagen-induced arthritis," Proc Natl Acad Sci USA, 89:9784 (1992).
Winter et al., "Humanized antibodies," Immunology Today, 14(6):243-246 (1993).
Winter et al., "Making Antibodies by Phage Display Technology," Annu. Rev. Immunol., 12:433-455 (1994).
Winterfield et al., "Psoriasis treatment: current and emerging directed therapies." Annals of the Rheumatic Diseases, 64 (2):1187-1190 (2005).
Wollina et al., "Treatment of recalcitrant psoriatic arthritis with anti-tumor necrosis factor-alpha antibody," J. Eur. Acad. Dermatology and Venereology, 16(2):127-129 (2002).
Woon et al., "Kinetics of cytokine production in experimental autoimmune anterior uveitis (EAAU)," Current Eye Research, 17:955 (1998).
World Health Organization Informed Consent Form Template, available from http://www.who.int/rpc/research_ethics/informed_consent/en/.
World Medical Association Declaration of Helsinki (2002).

(56) References Cited

OTHER PUBLICATIONS

Yakeuchi et al., "Anti-TNF Therapy in Rheumor Arthritis," Japanese Journal of Clinical Immunology, 27(1):7-15 (2004).
Yamauchi et al., "Adalimubab in the Management of Hidradenitis Suppurativa," J Am Acad. Deam., AB41:P504 (2007).
Yazici et al., "A preliminary study of etanercept in the treatment of severe, resistant psoriatic arthritis," Clinical and Experimental Rheumatology, 18:732-734 (2000).
Yazici, et al., "Etanercept in the treatment of severe, resistant psoriatic arthritis: Continued efficacy and changing patterns of use after two years," Clin Exp Rheumatol. Jan.-Feb. 2002;20(1):115.
Zabraniecki et al., "TNF alpha inhibition in psoriatic arthritis: cause for hope," Joint Bone Spine Mar;68(2):106-8 (2001).
Zhou et al., "Pharmacokinetics and Safety of Golimumab, a Fully Human Anti-TNF-a Monoclonal Antibody, in Subjects With Rheumatoid Arthritis," J. Clin. Pharmacol., 47:383-396, 2007.
Zou et al., "Immunological basis for the use of TNF-alpha-blocking agents in ankylosing spondylitis and immunological changes during treatment," Clin Exp Rheumatol. Nov.-Dec.•20(6 Suppl 2S):S34-7 (2002).

\* cited by examiner

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: D2E7 light chain variable region

<400> SEQUENCE: 1

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105
```

<210> SEQ ID NO 2
<211> LENGTH: 121
<212> TYPE: PRT
<213> ORGANISM: Artificial Sequence
<220> FEATURE:
<223> OTHER INFORMATION: D2E7 heavy chain variable region

<400> SEQUENCE: 2

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

<210> SEQ ID NO 3
<211> LENGTH: 9
<212> TYPE: PRT
<213> ORGANISM: Artificial Sequence
<220> FEATURE:
<223> OTHER INFORMATION: D2E7 light chain variable region CDR3
<220> FEATURE:
<221> NAME/KEY: VARIANT
<222> LOCATION: )9
<223> OTHER INFORMATION: Xaa = Any Amino Acid

```
<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: D2E7 heavy chain variable region CDR3
<220> FEATURE:
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: D2E7 heavy chain variable region CDR1

<400> SEQUENCE: 8

Asp Tyr Ala Met His
1               5

<210> SEQ ID NO 9
<211> LENGTH: 107
```

```
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
```

```
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial Sequence
```

```
<220> FEATURE:
<223> OTHER INFORMATION: VLLOG7 light chain variable region CDR3

<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
 1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
 1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
 1               5

<210> SEQ ID NO 24
<211> LENGTH: 9
<212> TYPE: PRT
<213> ORGANISM: Artificial Sequence
<220> FEATURE:
```

-continued

```
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: LOE7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3
```

```
<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10

<210> SEQ ID NO 36
<211> LENGTH: 321
<212> TYPE: DNA
<213> ORGANISM: Artificial Sequence
<220> FEATURE:
<223> OTHER INFORMATION: D2E7 light chain variable region
```

```
-continued

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial Sequence
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

USE OF TNFα INHIBITOR

RELATED APPLICATIONS

This application claims priority to U.S. Provisional Appln. No. 60/681,645, which was filed on May 16, 2005.

This application is related to U.S. Pat. Nos. 6,090,382, 6,258,562, and 6,509,015. This application is also related to U.S. patent application Ser. No. 09/801,185, filed Mar. 7, 2001; U.S. patent application Ser. No. 10/163,657, filed Jun. 5, 2002; and U.S. patent application Ser. No. 10/422,287, filed Apr. 26, 2002; U.S. patent application Ser. No. 10/525,292, filed Aug. 16, 2002; U.S. patent application Ser. No. 10/693,233, filed Oct. 24, 2003; U.S. patent application Ser. No. 10/622,932, now U.S. Patent Application Publication No. 2004/0126372, filed Jul. 18, 2003; U.S. patent application Ser. No. 10/623,039, filed Jul. 18, 2003; U.S. patent application Ser. No. 10/623,076, filed Jul. 18, 2003; U.S. patent application Ser. No. 10/623,065, filed Jul. 18, 2003; U.S. patent application Ser. No. 10/622,928, filed Jul. 18, 2003; U.S. patent application Ser. No. 10/623,075, filed Jul. 18, 2003; U.S. patent application Ser. No. 10/623,035, filed Jul. 18, 2003; U.S. patent application Ser. No. 10/622,683, filed Jul. 18, 2003; U.S. patent application Ser. No. 10/622,205, filed Jul. 18, 2003; U.S. patent application Ser. No. 10/622,210, filed Jul. 18, 2003; and U.S. patent application Ser. No. 10/623,318, filed Jul. 18, 2003. This application is also related to PCT/US05/12007, filed Apr. 11, 2005. The entire contents of each of these patents and patent applications, including the above-mentioned U.S. Patent Application Publication No. 2004/0126372, are hereby incorporated herein by reference. The above-mentioned International Patent Application No. PCT/US05/12007 includes the same specification (excluding the claims) as U.S. Patent Application No. 2006/0009385, and the specification of U.S. Patent Application No. 2006/0009385 (excluding the claims) is incorporated herein by reference in its entirety.

BACKGROUND OF THE INVENTION

Polyarthritis may be erosive or non-erosive. In the erosive form, the underlying disease process erodes the cartilage; in the non-erosive form, the cartilage is not affected. Erosive polyarthritis is an inflammatory disease of joints that results in tissue destruction and erosion within the affected joint. Erosive polyarthritis occurs in many patients having inflammatory disorders, including psoriatic arthritis, spondylarthropathies, such as ankylosing spondylitis, and juvenile rheumatoid arthritis. Many of the current treatments of disorders in which erosive polyarthritis is a manifestation fail to focus on decreasing radiographic progression of joint disease.

SUMMARY OF THE INVENTION

There is a need to treat erosive polyarthritis in a safe and effective manner. While traditional treatments of erosive polyarthritis, such as administration of DMARDs, may delay disease progression, traditional treatments may be slow to become effective, may lose efficacy with time, and may be associated with potentially serious toxic effects. The present invention provides a safe and effective means for treating erosive polyarthritis and slowing the progression of joint disease.

The present invention includes methods of treating erosive polyarthritis comprising administering TNF inhibitors. The invention also provides a method for treating a human subject suffering from erosive polyarthritis, comprising administering to the subject an anti-TNFα antibody, such that erosive polyarthritis is treated. Kits and articles of manufacture comprising a TNFα inhibitor are also included in the invention.

In one embodiment, the TNFα inhibitor is selected from the group consisting of an anti-TNFα antibody, or an antigen-binding portion thereof, a TNF fusion protein, or a recombinant TNF binding protein. In one embodiment, the TNF fusion protein is etanercept. In another embodiment, the anti-TNFα antibody, or antigen-binding portion thereof, is an antibody selected from the group consisting of a humanized antibody, a chimeric antibody, and a multivalent antibody. In one embodiment, the anti-TNFα antibody, or antigen-binding portion thereof, is infliximab, golimumab, or adalimumab. In still another embodiment, the anti-TNFα antibody, or antigen-binding portion thereof, is a human antibody.

The invention provides a method for treating a human subject suffering from erosive polyarthritis, comprising administering to the subject a TNFα antibody, or antigen-binding portion thereof, such that erosive polyarthritis is treated.

In one embodiment, the TNFα antibody, or antigen-binding portion thereof, is an antibody selected from the group consisting of a humanized antibody, a chimeric antibody, and a multivalent antibody. In another embodiment, the TNFα antibody, or antigen-binding portion thereof, is infliximab or golimumab.

In one embodiment, the TNFα antibody, or antigen-binding portion thereof, is a human antibody. In one embodiment, the human antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. In another embodiment, the human antibody, or an antigen-binding portion thereof, has the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In still another embodiment, the human antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7, or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In yet another embodiment, the human antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2. In one embodiment, the human antibody, or an antigen-binding portion thereof, is adalimumab.

In one embodiment, the TNFα antibody, or antigen-binding portion thereof, is administered to the subject on a biweekly dosing regimen.

In one embodiment, the subject has a disorder in which TNFα activity is detrimental. In one embodiment, the disorder in which TNFα activity is detrimental is selected from the group consisting of psoriatic arthritis, ankylosing spondylitis, and juvenile rheumatoid arthritis. In another embodiment, the disorder in which TNFα activity is detrimental is psoriatic arthritis. In still another embodiment, the disorder in which TNFα activity is detrimental is rheumatoid arthritis.

In one embodiment, the invention includes further comprising administering an additional therapeutic agent to the subject. In one embodiment, the additional therapeutic agent is methotrexate. In another embodiment, the additional therapeutic agent is a Disease Modifying Anti-Rheumatic Drug (DMARD) or a Nonsteroidal Antiinflammatory Drug (NSAID) or a steroid, or any combination thereof.

The invention includes a method for testing the efficacy of a TNFα antibody, or antigen-binding portion thereof, for decreasing radiographic progression of joint disease associated with erosive polyarthritis. In one embodiment, the method for testing the efficacy of a TNFα antibody, or antigen-binding portion thereof, comprises determining the efficacy of the TNFα antibody, or antigen-binding portion thereof, using a modified Total Sharp Score (mTSS) of a patient population having joint disease associated with erosive polyarthritis and a mTSS of the patient population following administration of the TNFα antibody, or antigen-binding portion thereof, wherein no change or a decrease in the mTSS indicates that the TNFα antibody, or antigen-binding portion thereof, is efficacious for decreasing radiographic progression of joint disease associated with erosive polyarthritis. In one embodiment, the decrease in the mTSS is about −0.2.

In one embodiment, the patient population also has a disorder in which TNFα is detrimental. In one embodiment, the disorder in which TNFα activity is detrimental is selected from the group consisting of psoriatic arthritis, ankylosing spondylitis, and juvenile rheumatoid arthritis.

In one embodiment, the TNFα antibody, or antigen-binding portion thereof, is an antibody selected from the group consisting of a humanized antibody, a chimeric antibody, and a multivalent antibody. In one embodiment, the TNFα antibody, or antigen-binding portion thereof, is infliximab or golimumab. In another embodiment, the TNFα antibody, or antigen-binding portion thereof, is a human antibody. In one embodiment, the human antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less.

In another embodiment, the human antibody, or an antigen-binding portion thereof, has the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7, or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In still another embodiment, the human antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7, or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11.

In another embodiment, the human antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2. In still another embodiment of the invention, the human antibody, or an antigen-binding portion thereof, is adalimumab.

In one embodiment of the invention, the TNFα antibody, or antigen-binding portion thereof, is administered to the subject on a biweekly dosing regimen. In one embodiment, antibody, or antigen-binding portion thereof, is administered in combination with an additional therapeutic agent, including, for example methotrexate The invention describes a method for monitoring the effectiveness of a TNFα antibody, or antigen-binding portion thereof, for the treatment of erosive polyarthritis in a human subject comprising determining the effectiveness of the TNFα antibody, or antigen-binding portion thereof, using a baseline modified Total Sharp Score (mTSS) of a patient population having erosive polyarthritis and a mTSS score of a patient population following administration of the TNFα antibody, or antigen-binding portion thereof, wherein a result selected from the group consisting of a decrease in the mTSS in about 9-27% of the patient population; no change in the mTSS in about 65-73% of the patient population; and an increase in the mTSS in about 9-28% of the patient population, indicates that the TNFα antibody, or antigen-binding portion thereof, is effective at treating erosive polyarthritis.

In one embodiment of the invention, the TNFα antibody, or antigen-binding portion thereof, is an antibody selected from the group consisting of a humanized antibody, a chimeric antibody, and a multivalent antibody. In one embodiment, the TNFα antibody, or antigen-binding portion thereof, is infliximab or golimumab. In another embodiment, the TNFα□ antibody, or antigen-binding portion thereof, is a human antibody.

In another embodiment, the human antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In still another embodiment, the human antibody, or an antigen-binding portion thereof, is adalimumab.

The invention also includes a method for testing the efficacy of a TNFα antibody, or antigen-binding portion thereof, to treat erosive polyarthritis associated with psoriatic arthritis, comprising determining the efficacy of the TNFα antibody, or antigen-binding portion thereof, using a baseline modified Total Sharp Score (mTSS) and either a baseline Psoriasis Area and Severity Index (PASI) score or a baseline ACR score of a patient population having erosive polyarthritis in comparison with the mTSS and either the PASI or the ACR score of the patient population following administration of the NFα antibody, or antigen-binding portion thereof, wherein no change or a decrease in the mTSS and either an ACR20 response achieved in at least about 57% or a PASI 50 response achieved in at least about 75% of the patient population, indicates that the TNFα antibody, or antigen-binding portion thereof, is efficacious for the treatment of erosive polyarthritis associated with psoriatic arthritis. In one embodiment, an ACR50 response is achieved in at least about 39% of the patient population. In another embodiment, an ACR70 response is achieved in at least about 23% of the patient population. In still another embodiment, a PASI75 response is achieved in at least about 59% of the patient population. In yet another embodiment, a PASI90 response is achieved in at least about 42% of the patient population. In one embodiment, the TNFα antibody, or antigen-binding portion thereof, is adalimumab.

The invention describes a method for treating erosive polyarthritis comprising administering to a subject having erosive polyarthritis, adalimumab on a biweekly dosing regimen. In one embodiment, the dose of adalimumab is about 40 mg.

The invention also includes a kit comprising a pharmaceutical composition comprising a TNFα antibody, or an antigen-binding portion thereof, and a pharmaceutically acceptable carrier, and instructions for administration of the pharmaceutical composition for the treatment of erosive polyarthritis. In one embodiment, the pharmaceutical composition comprises the TNFα antibody, or antigen-binding portion thereof, adalimumab. In one embodiment, pharmaceutical composition comprises about 40 mg of adalimumab. In another embodiment, the kit further comprises an additional therapeutic agent. In one embodiment, the additional therapeutic agent is methotrexate.

The invention describes an article of manufacture comprising a packaging material; a TNFα antibody, or antigen-binding portion thereof; and a label or package insert contained within the packaging material indicating that the TNFα antibody, or antigen-binding portion thereof, can be used for the treatment of erosive polyarthritis.

The invention also includes an article of manufacture comprising a packaging material; a TNFα antibody, or antigen-binding portion thereof; and a label or package insert contained within the packaging material indicating that the TNFα antibody, or antigen-binding portion thereof, can be used for to inhibit radiographic progression of joint disease.

In one embodiment, the article of manufacture comprises an antibody selected from the group consisting of a humanized antibody, a chimeric antibody, and a multivalent antibody.

In one embodiment, the TNFα antibody, or antigen-binding portion thereof, is infliximab or golimumab. In another embodiment, the TNFα antibody, or antigen-binding portion thereof, is a human antibody. In one embodiment, the human antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. In another embodiment, the human antibody, or an antigen-binding portion thereof, is adalimumab.

FIGURES

Figure 6:
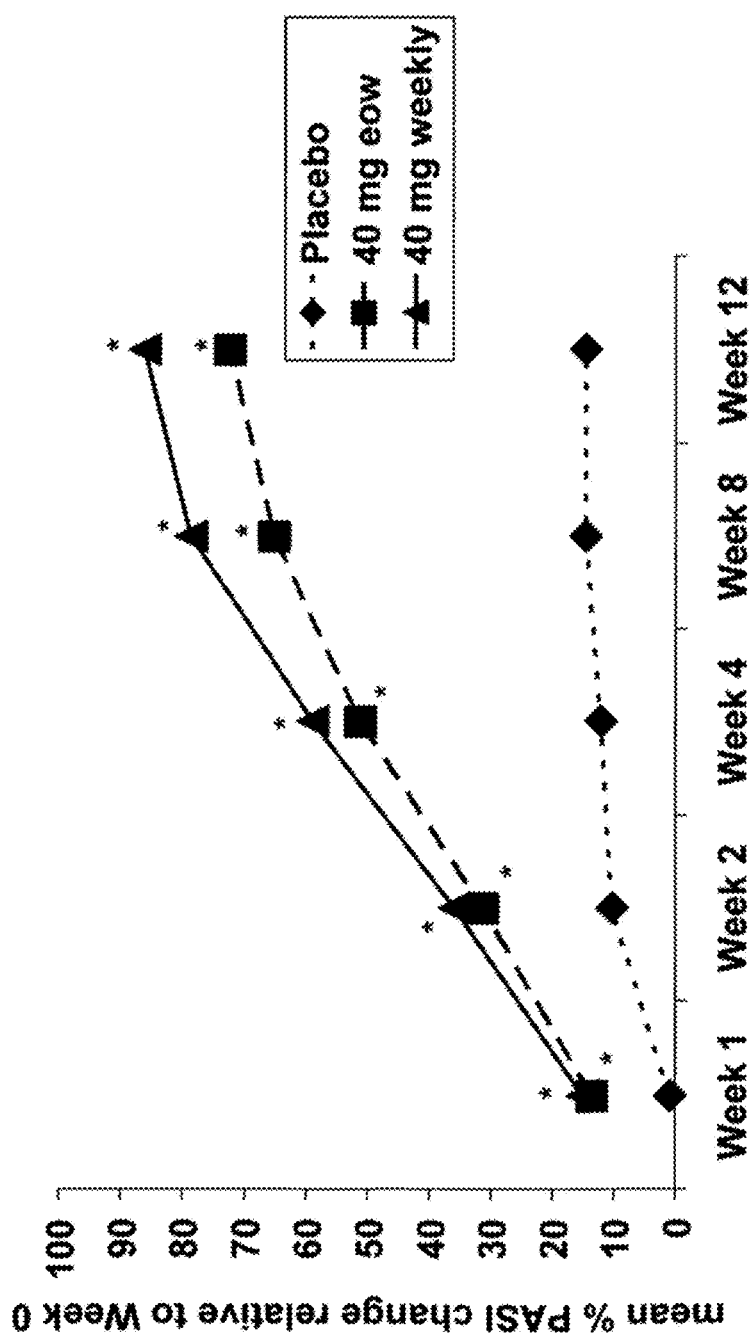

FIG. 6 provides results of the mean percentage PASI (Psoriasis Area and Severity Index) improvement over a 12 week treatment (eow=every other week; *=p<0.001 vs. placebo).

Figure 7:
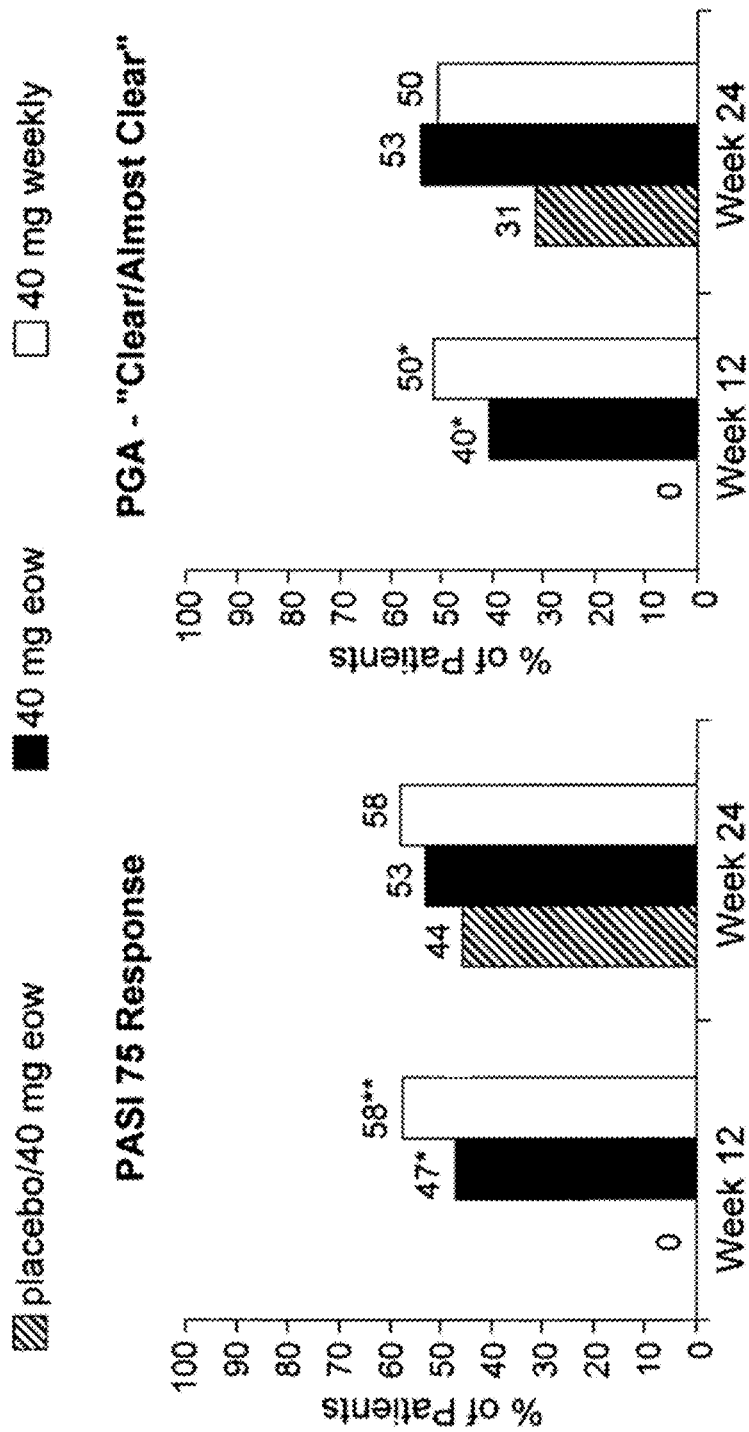

FIG. 7 shows a comparative graph of the efficacy response at week 12 and week 24 for patients with psoriasis and PsA.

Figure 8:
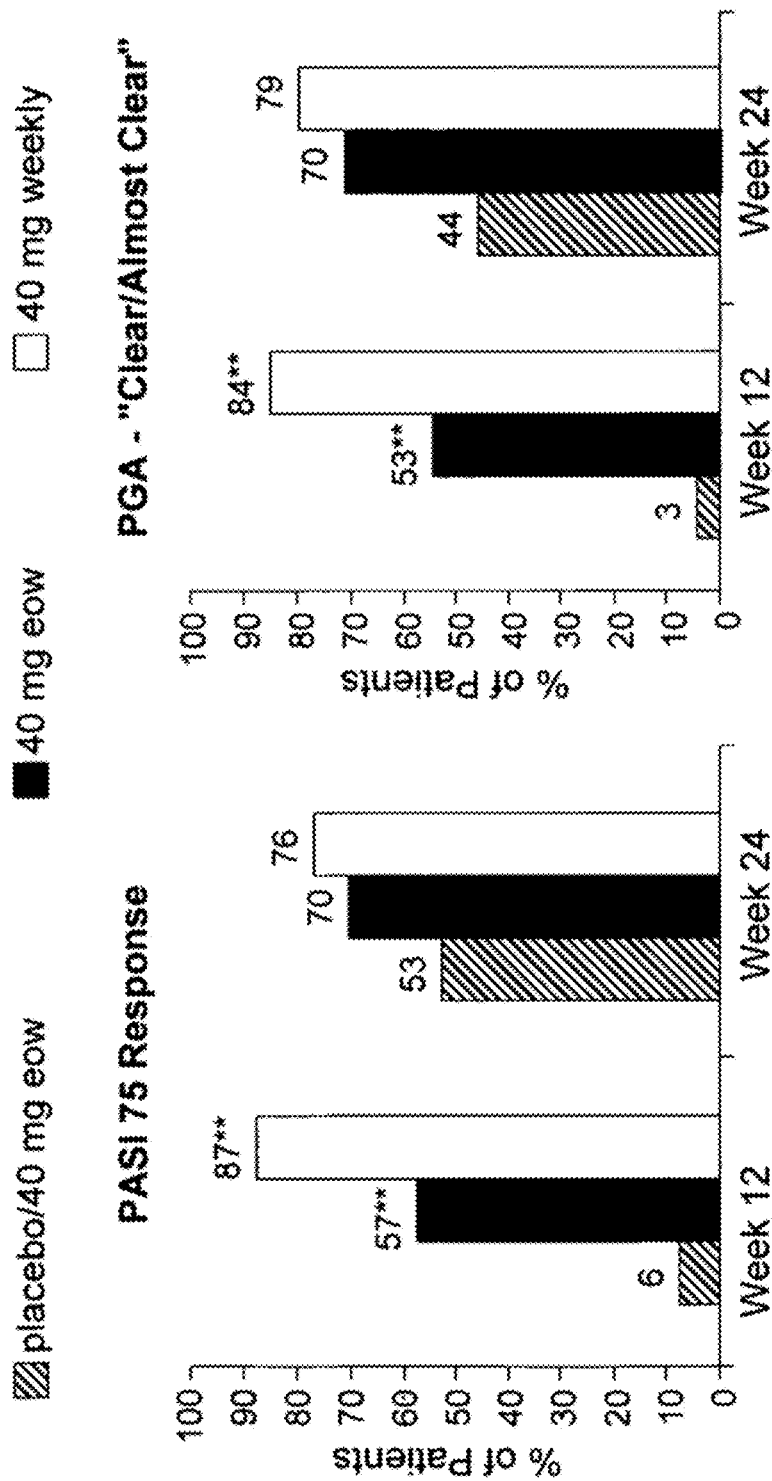

FIG. 8 shows a comparative graph of the efficacy response at week 12 and week 24 for patients with psoriasis and without PsA.

DETAILED DESCRIPTION OF THE INVENTION

I. Definitions

In order that the present invention may be more readily understood, certain terms are first defined.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent which interferes with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090, 382 as D2E7). Additional TNF antibodies which can be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J Immunol.* 148, 1547-1553 (1992).

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-hTNFα antibody contains no other sequences encoding other VH regions that bind antigens other than hTNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "dose," as used herein, refers to an amount of TNFα inhibitor which is administered to a subject.

The term "multiple-variable dose" includes different doses of a TNFα inhibitor which are administered to a subject for therapeutic treatment. "Multiple-variable dose regimen" or "multiple-variable dose therapy" describe a treatment schedule which is based on administering different amounts of TNFα inhibitor at various time points throughout the course of treatment. In one embodiment, the invention describes a multiple-variable dose method of treatment of erosive polyarthritis comprising an induction phase and a treatment phase, wherein a TNFα inhibitor is administered at a higher dose during the induction phase than the treatment phase. Multiple-variable dose regimens are described in PCT application no. PCT/US05/12007.

The term "dosing", as used herein, refers to the administration of a substance (e.g., an anti-TNFα antibody) to achieve a therapeutic objective (e.g., the treatment of erosive polyarthritis).

The terms "biweekly dosing regimen", "biweekly dosing", and "biweekly administration", as used herein, refer to the time course of administering a substance (e.g., an anti-TNFα antibody) to a subject to achieve a therapeutic objective (e.g., the treatment of erosive polyarthritis). The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions. In one embodiment, the invention provides a combination therapy for treating erosive polyarthritis comprising administering an anti-TNF antibody.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "kit" as used herein refers to a packaged product or article of manufacture comprising components. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the TNFα antibody, or antigen-binding portion thereof. In one embodiment the kit of the invention includes the formulation comprising the human antibody D2E7, as described in PCT/IB03/04502 and U.S. application Ser. No. 10/222,140.

Various aspects of the invention are described in further detail herein.

II. TNFα Inhibitors

This invention provides a method of treating erosive polyarthritis in which the administration of a TNFα inhibitor e.g., a TNFα antibody, or antigen-binding portion thereof, is beneficial. In one embodiment, these methods include administration of isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies.

In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein.

The most preferred recombinant, neutralizing antibody used in the invention is referred to herein as D2E7, also referred to as HUMIRA® and adalimumab (the amino acid sequence of the D2E7 VL region is shown in SEQ ID NO: 1; the amino acid sequence of the D2E7 VH region is shown in SEQ ID NO: 2). The properties of D2E7 (HUMIRA®) have been described in Salfeld et al., U.S. Pat. Nos. 6,090,382, 6,258,562, and 6,509,015, which are each incorporated by reference herein. Other examples of TNFα inhibitors include chimeric and humanized murine anti-hTNFα antibodies which have undergone clinical testing for treatment of rheumatoid arthritis (see e.g., Elliott et al. (1994) *Lancet* 344:1125-1127; Elliot et al. (1994) *Lancet* 344:1105-1110; Rankin et al. (1995) *Br. J. Rheumatol.* 34:334-342). In another embodiment, the anti-TNFα antibody is multivalent.

In one embodiment, the method of treating erosive polyarthritis of the invention includes the administration of D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity. In one embodiment, the invention provides a method for treating erosive polyarthritis with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1 \times 10^{-8}$ M or less, even more preferably with an IC$_{50}$ of $1 \times 10^{-9}$ M or less and still more preferably with an IC$_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to methods of treating erosive polyarthritis by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7, or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the invention provides methods of treating erosive polyarthritis by the administration of an isolated human antibody, or antigen-binding portion thereof. The antibody or antigen-binding portion thereof preferably contains the following characteristics:

a) dissociates from human TNFα with a $K_{off}$ rate constant of $1 \times 10^{-3}$ $s^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7, or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ $s^{-1}$ or less. Even more preferably, the antibody, or antigen-binding portion thereof, dissociates from human TNFα with a $K_{off}$ of $1 \times 10^{-4}$ $s^{-1}$ or less.

In yet another embodiment, the invention provides a method of treating erosive polyarthritis by administration of an isolated human antibody, or antigen-binding portion thereof. The antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7, or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_{\kappa}I$ human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H3$ human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the invention provides a method of treating erosive polyarthritis by the administration of an isolated human antibody, or antigen-binding portion thereof. The antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention describes a method of treating erosive polyarthritis in which the administration of an anti-TNFα antibody wherein the antibody is an isolated human antibody, or an antigen-binding portion thereof. The antibody or antigen-binding portion thereof preferably contains D2E7-related VL and VH CDR3 domains, for example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the invention can also be modified. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1-C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat erosive polyarthritis and TNFα-related disorders of the invention by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield and Morrison (1991) *J. Exp. Med.* 173:1483-1491; and Lund et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel et al. (eds.) *Current Protocols in Molecular Biology*, Greene Publishing Associates, (1989) and in U.S. Pat. No. 4,816,397 by Boss et al.

To express D2E7 or a D2E7-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat et al. (1991) *Sequences of Proteins of Immunological Interest, Fifth Edition*, U.S. Department of Health and Human Services, NIH Publication No. 91-3242; Tomlinson et al. (1992) "The Repertoire of Human Germline $V_H$ Sequences Reveals about Fifty Groups of $V_H$ Segments with Different Hypervariable Loops" *J. Mol. Biol.* 227:776-798; and Cox et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used.

The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in Kaufman and Sharp (1982)*Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) EMBO J 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human antibodies with high affinity and a low off rate constant for hTNFα are also described in U.S. Pat. Nos. 6,090,382, 6,258,562, and 6,509,015, each of which is incorporated by reference herein.

The TNFα inhibitor may also be a TNF fusion protein, e.g., etanercept (Enbrel®, Amgen; described in WO 91/03553 and WO 09/406476, incorporated by reference herein). In another embodiment, the TNFα inhibitor is a recombinant TNF binding protein (r-TBP-I) (Serono).

III. Treatment of Erosive Polyarthritis

The invention provides methods of treating erosive polyarthritis comprising administering a TNFα inhibitor, including, for an example, a TNFα antibody, to a subject having erosive polyarthritis. The invention also describes methods for determining the efficacy of a TNFα inhibitor for the treatment of erosive polyarthritis. Preferably, the TNFα is human TNFα and the subject is a human subject. In one embodiment, the TNFα inhibitor is adalimumab, also referred to as HUMIRA® or D2E7. The use of TNFα inhibitors, including antibodies and antibody portions, in the treatment of erosive polyarthritis, as well as methods for determining the efficacy of a TNFα inhibitor for the treatment of erosive polyarthritis, is discussed further below:

The term "polyarthritis" generally refers to inflammation, i.e., swelling, tenderness, or warmth, at two or more joints of a subject.

As used herein, the term "erosive polyarthritis" refers to a subject who has polyarthritis which is damaging to the joint.

The invention provides a method for treating erosive polyarthritis comprising administration of a TNFα inhibitor, including, for an example, a TNFα antibody. The invention also provides a method for inhibiting radiographic progression of joint disease associated with erosive polyarthritis. Methods for administering a TNFα antibody, or an antigen-binding portion thereof, for the treatment of erosive polyarthritis are described in more detail below.

The invention provides a method for determining the efficacy of an anti-TNFα treatment for erosive polyarthritis. Measures for determining such efficacy include tests which determine whether joint destruction or erosion is improved following treatment. For example, the Total Modified Sharp Score (mTSS) of a subject may be used to determine improvements in erosive polyarthritis in the subject. The mTSS may also be used as an assay to determine the efficacy of a treatment for erosive polyarthritis.

A Sharp score is an X-ray measurement in changes in total joint damage as assessed by bone erosions and joint space narrowing (Sharp et al. (1971)*Arthritis & Rheumatism* 14:706; Sharp et al. (1985) *Arthritis & Rheumatism* 28:16). The mTSS is a measure of the extent and severity of joint damage based on evaluations of x-rays of patients' hands and feet. Joints are scored for both joint erosions and joint space narrowing. The mTSS is the sum of the erosion score (ES) and the joint space narrowing (JSN) score and has, for example, a range of about 0 to about 398, where 0=no damage. The ES is the sum of joint scores collected for 46 joints and has a range, for example, of about 0 to about 230. The JSN is the sum of joint scores collected for 42 joints and has a range, for example, of about 0 to about 168. A score of 0 would indicate no change. In one embodiment of the invention, the mTSS is determined by combining the joint space narrowing score having a range of about 0-192 and an erosion score having a range of about 0-378.

An improved or constant mTSS demonstrates that the TNFα inhibitor is effective for treating erosive polyarthritis. In one embodiment, efficacy of a TNFα inhibitor for the treatment of erosive polyarthritis is evidenced by a lack of progression of joint disease, e.g., no change in Sharp score, in mTSS over time in a subject having erosive polyarthritis. In another embodiment, efficacy of a TNFα inhibitor for the treatment of erosive polyarthritis is evidenced by a decrease in the radiographic progression of joint disease, e.g., decrease in Sharp score, in mTSS over time in a subject having erosive polyarthritis.

In one embodiment, the overall change in the mTSS between baseline and a time period following treatment with a TNFα inhibitor is between about 0.9 and about −0.2. In another embodiment, the overall change in the mTSS between baseline and a time period following treatment with a TNFα inhibitor is between about 0.5 and about −0.2. In still another embodiment, the overall change in the mTSS between baseline and a time period following treatment with a TNFα inhibitor is between about 0.2 and about −0.2.

It should be noted that ranges intermediate to the above recited scores, e.g., about −0.1 to about 0.3, are also intended to be part of this invention. For example, ranges of values using a combination of any of the above recited values as upper and/or lower limits are intended to be included.

While treatment of an inflammatory disease with an anti-inflammatory agent may result in clinical improvements following treatment, there may still be progressive joint damage resulting from erosive polyarthritis (Gladman et al. (1990) *J Rheumatol* 17:809; Hanly et al. (1988) *Ann Rheum Dis* 47:386). Thus, it is a feature of this invention to provide a method for treating erosive polyarthritis which may be associated with another disorder. In a preferred embodiment, the invention includes treatment of erosive polyarthritis associated with a disorder in which TNFα activity is detrimental, including, but not limited to, rheumatoid arthritis (including juvenile rheumatoid arthritis), Crohn's disease, psoriasis, psoriatic arthritis, and ankylosing spondylitis. Erosive polyarthritis may also be associated with multicentric reticulohistiocytosis (MRH) (Santilli et al. (2002) *Ann Rehum Dis* 61: 485).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of TNFα inhibitors for the treatment of erosive polyarthritis associated with specific disorders is discussed further below:

A. Autoimmune Diseases

In one embodiment, the invention includes treatment of erosive polyarthritis associated with an autoimmune disease. Erosive polyarthritis may be found in patients suffering from autoimmune diseases, including forms of arthritis such as rheumatoid arthritis and juvenile rheumatoid arthritis (Verloes (1998) *Med Genet.* 35:943). TNFα antibodies, such as adalimumab, may be used to treat autoimmune diseases, in particular those associated with erosive polyarthritis. Examples of such autoimmune conditions include rheumatoid arthritis, rheumatoid spondylitis, osteoarthritis and gouty arthritis, allergy, multiple sclerosis, autoimmune diabetes, autoimmune uveitis and nephrotic syndrome. Other examples of autoimmune conditions include multisystem autoimmune diseases and autoimmune hearing loss. Other examples of autoimmune disease are described in U.S. application Ser. No. 10/622,932, incorporated by reference herein.

Juvenile Rheumatoid Arthritis

Tumor necrosis factor has been implicated in the pathophysiology of juvenile arthritis, including juvenile rheumatoid arthritis (Grom et al. (1996) *Arthritis Rheum.* 39:1703; Mangge et al. (1995) *Arthritis Rheum.* 8:211). In one embodiment, the TNFα antibody of the invention is used to treat juvenile rheumatoid arthritis.

The term "juvenile rheumatoid arthritis" or "JRA" as used herein refers to a chronic, inflammatory disease which occurs before age 16 that may cause joint or connective tissue damage. JRA is also referred to as juvenile chronic polyarthritis and Still's disease.

JRA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JRA can also affect the internal organs.

JRA is often classified into three types by the number of joints involved, the symptoms, and the presence or absence of certain antibodies found by a blood test. These classifications help the physician determine how the disease will progress and whether the internal organs or skin is affected. The classifications of JRA include the following:

a. Pauciarticular JRA, wherein the patient has four or fewer joints are affected. Pauciarticular is the most common form of JRA, and typically affects large joints, such as the knees.

b. Polyarticular HRA, wherein five or more joints are affected. The small joints, such as those in the hands and feet, are most commonly involved, but the disease may also affect large joints.

c. Systemic JRA is characterized by joint swelling, fever, a light skin rash, and may also affect internal organs such as the heart, liver, spleen, and lymph nodes. Systemic JRA is also referred to as it Still's disease. A small percentage of these children develop arthritis in many joints and can have severe arthritis that continues into adulthood.

B. Spondyloarthropathies

In one embodiment, the invention includes treatment of erosive polyarthritis associated with a spondylarthopathy. Erosive polyarthritis may be found in patients suffering from inflammatory diseases, such as spondyloarthopathies, associated with detrimental TNFα activity (see e.g., Moeller et al. (1990) *Cytokine* 2:162; U.S. Pat. No. 5,231,024; European Patent Publication No. 260 610).

As used herein, the term "spondyloarthropathy" or "spondyloarthropathies" is used to refer to any one of several diseases affecting the joints of the spine, wherein such diseases share common clinical, radiological, and histological features. A number of spondyloarthopathies share genetic characteristics, i.e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthopathies include ank/ank transgenic mice, HLA-B27 transgenic rats (see Taurog et al. (1998) *The Spondylarthritides*. Oxford:Oxford University Press).

Examples of subjects who are at risk of having spondyloarthropathies include humans suffering from arthritis. Spondyloarthropathies can be associated with forms of arthritis, including rheumatoid arthritis. In one embodiment of the invention, a TNFα inhibitor is used to treat a subject who suffers from a spondyloarthropathy associated with erosive polyarthritis. Examples of spondyloarthropathies which can be treated with a TNFα inhibitor are described below:

Ankylosing Spondylitis (AS)

In one embodiment, the invention includes treatment of erosive polyarthritis associated with ankylosing spondylitis using a TNFα antibody, or antigen-binding portion thereof. Tumor necrosis factor has been implicated in the pathophysiology of ankylosing spondylitis (see Verjans et al. (1991) *Arthritis Rheum.* 34:486; Verjans et al. (1994) *Clin Exp Immunol.* 97:45; Kaijtzel et al. (1999) *Hum Immunol.* 60:140). Ankylosing spondylitis (AS) is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA) and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) *ACR 66th Annual Scientific Meeting* Abstract).

Psoriatic Arthritis

In one embodiment, the invention includes treatment of erosive polyarthritis associated with psoriatic arthritis using a TNFα antibody, or antigen-binding portion thereof. Tumor necrosis factor has been implicated in the pathophysiology of psoriatic arthritis (PsA) (Partsch et al. (1998) *Ann Rheum Dis.* 57:691; Ritchlin et al. (1998) *J Rheumatol.* 25:1544). As referred to herein, psoriatic TNFα has been implicated in activating tissue inflammation and causing joint destruction in rheumatoid arthritis (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

Psoriatic arthritis refers to chronic inflammatory arthritis which is associated with psoriasis, a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. A TNFα antibody, or antigen-binding fragment thereof, can be used for treatment of erosive polyarthritis associated with PsA.

PsA is sometimes associated with arthritis mutilans. Arthritis mutilans refers to a disorder which is characterized by excessive bone erosion resulting in a gross, erosive deformity which mutilates the joint.

Characteristic radiographic features of PsA include joint erosions, joint space narrowing, bony proliferation including periarticular and shaft periostitis, osteolysis including "pencil in cup" deformity and acro-osteolysis, ankylosis, spur formation, and spondylitis (Wassenberg et al. (2001) *Z Rheumatol* 60:156). Unlike rheumatoid arthritis (RA), joint involvement in PsA is often asymmetrical and may be oligoarticular; osteoporosis is atypical. Although erosive changes in early PsA are marginal as in RA, they become irregular and ill defined with disease progression because of periosteal bone formation adjacent to the erosions. In severe cases, erosive changes may progress to development of pencil in cup deformity or gross osteolysis (Gold et al. (1988) *Radiol Clin North Am* 26:1195; Resnick et al. (1977)) *J Can Assoc Radiol* 28:187). Asymmetrical erosions may be visible radiographically in the carpus and in the metacarpophalangeal (MCP), proximal interphalangeal (PIP), and distal interphalangeal (DIP) joints of the hands, but the DIP joints are often the first to be affected. Abnormalities are seen in the phalangeal tufts and at the sites of attachments of tendons and ligaments to the bone. The presence of DIP erosive changes may provide both sensitive and specific radiographic findings to support the diagnosis of PsA. Also, the hands tend to be involved much more frequently than the feet with a ratio of nearly 2:1.

Other examples of spondyloarthropathies are described in U.S. application Ser. No. 10/622,932, incorporated by reference herein.

C. Skin and Nail Disorders

In one embodiment, the invention includes treatment of erosive polyarthritis associated with skin and nail disorders. As used herein, the term "skin and nail disorder in which TNFα activity is detrimental" is intended to include skin and/or nail disorders and other disorders in which the presence of TNFα in a subject suffering from the disorder has been shown to be or is suspected of being either responsible for the pathophysiology of the disorder or a factor that contributes to a worsening of the disorder, e.g., psoriasis. Accordingly, skin and nail disorders in which TNFα activity is detrimental are disorders in which inhibition of TNFα activity is expected to alleviate the symptoms and/or progression of the disorder. The use of the antibodies, antibody portions, and other TNFα inhibitors for the treatment of specific skin and nail disorders is discussed further below. In certain embodiments, the antibody, antibody portion, or other TNFα inhibitor of the invention is administered to the subject in combination with another therapeutic agent, as described below. In one embodiment, a TNFα antibody is administered to the subject in combination with another therapeutic agent for the treatment of erosive polyarthritis associated with psoriasis and the treatment of psoriasis associated with arthritis.

Psoriasis

Tumor necrosis factor has been implicated in the pathophysiology of psoriasis (Takematsu et al. (1989) *Arch Dermatol Res.* 281:398; Victor and Gottlieb (2002) *J Drugs Dermatol.* 1(3):264). Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease.

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually located on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof. In one embodiment, the TNFα inhibitor of the invention is administered in combination with or the presence of one of these common treatments. Additional therapeutic agents which can also be combined with the TNFα inhibitor for treatment of psoriasis are described in more detail below.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

In one embodiment of the invention, a TNFα inhibitor is used to treat psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Specific types of psoriasis included in the treatment methods of the invention include chronic plaque psoriasis, guttate psoriasis, inverse psoriasis, and pustular psoriasis. Other examples of psoriasis and other types of skin and nail disorders are described in U.S. application Ser. No. 10/622,932 (U.S. Pat. Publ. 2004/0126372), incorporated by reference herein.

Methods for determining the efficacy of a TNFα inhibitor for the treatment of erosive polyarthritis in association a disorder in which TNFα activity is detrimental include any assay which measures the degree of joint destruction, including joint space narrowing and/or joint erosion. In one embodiment, joint destruction is measured using radiography. Such assays may be used to examine the efficacy of the TNFα inhibitor by determining whether an improvement occurs in a subject or patient population treated with the TNFα inhibitor. Generally, improvements are determined by comparing a baseline score determined prior to treatment, and a score determined at a time following treatment with the TNFα inhibitor.

Additional improvements in arthritic conditions, such as Ra, PsA, and JRA, may be determined by measuring the ACR response. ACR thresholds, e.g., ACR20, ACR50, ACR70, may be used for defining improvement in RA and PsA, and indicate the percentage improvement in seven disease activity measures. Criteria include percentage improvement in tender and swollen joint count and improvement of at least 3 of the following criteria: patient pain assessment, patient global assessment, physician global assessment, patient self-assessed disability, or laboratory measures of disease activity (i.e., erythrocyte sedimentation rate or C-reactive protein level) (Felson et al. (1993) *Arthritis Rheum.* 36(6):729).

Other assays used to determine improvement for a given therapy for the treatment of RA, JRA, and PsA, include the EULAR response, DAS score, FACIT-F, HAQ score, and SJC and/or TJC counts.

The EULAR criteria uses a DAS for defining response. Response is defined as both: (a) change in disease activity from baseline and (b) the level of disease activity reached during follow-up. Criteria used to define DAS include: Ritchie articular index, swollen joint count (44-joint count), erythrocyte sedimentation rate, and Health Assessment Questionnaire. A modified version of the DAS criteria, DAS28, uses a 28-joint count for swollen and tender joints. Response is defined as a combination of a significant change from baseline and the level of disease activity attained. Good response is defined as a significant decrease in DAS (>1.2) and a low level of disease activity (< or =2.4). Non-response is defined as a decrease < or =0.6, or a decrease >0.6 and < or =1.2 with an attained DAS>3.7. Any other scores are regarded as moderate responses.

The DAS is a score is based on the Ritchie articular index, a 44 swollen joint count, ESR, and a general health assessment on a VAS. Range varies from 1 to 9. Serial measurements of the DAS and DAS28 are strong predictors of physical disability and radiological progression, and both indices are sensitive discriminators between patients with high and low disease activity and between active and placebo treated patient groups.

FACIT-F (Functional Assessment of Chronic Illness Therapy—Fatigue) is a validated questionnaire designed to measure patients' assessment of fatigue-related factors in chronic illness (see Cella and Webster (1997) *Oncology (Huntingt).* 11:232 and Lai et al. (2003) *Qual Life Res.* 12(5):485).

The Health Assessment Questionnaire (HAQ) is a validated questionnaire designed to assess patients' ability to perform activities of daily living, particularly in adult arthritics. Instrument consists of the HAQ Disability Index (20 items), Pain Scale (1 item), and Global Health Status (1 item) that measure disability/physical functioning and quality of life (Fries et al. (1982) *J Rheumatol.* 9(5):789).

Swollen and tender joints (SJC and TJC) are the most characteristic features of RA, and disease severity is directly related to the number of swollen and tender joints. Counting swollen and tender joints is a key component of the clinical assessment of RA.

Improvements in PsA and psoriasis may also be determined using the PASI response, DLQI, and the BSA score. DLQI (Dermatology Life Quality Index) is a health-related quality of life measure widely used for a variety of dermatological diseases, including PsA and psoriasis. The body Surface Area (BSA) score provides a measurement of surface area based on height and weight and expressed in $m^2$. The PASI (Psoriasis Area and Severity Index) is a composite measure of the erythema, induration, desquamation and body surface area that is affected by psoriasis for a particular patient. Patients are evaluated for head, trunk, upper and lower limb involvement. Scores range from 0 (clear) to 72 (maximum severity).

Improvements in treatment for PsA may also be measured using the PsARC (Psoriatic Arthritis Response Criteria), which provides a clinical measure of the change in tender and swollen joint scores, along with a series of global assessments of disease activity.

Improvements in AS may be measured by using any number of instruments to evaluate various AS symptoms. Some of the commonly used scales include the Assessment in Ankylosing Spondylitis (ASAS), the Bath Ankylosing Spondylitis Disease Activity Index (BASDAI) (Garrett et al. (1994) *J Rheumatol* 21:2286), the Bath Ankylosing Spondylitis Metrology Index (BASMI) (Jenkinson et al. (1994) *J Rheumatol* 21:1694), and the Bath Ankylosing Spondylitis Functional Index (BASFI) (Calin et al. (1994) *J Rheumatol* 21:2281). These indices can be used to monitor a patient over time and to determine improvement. Additional description measurements for assessing improvements in AS are described in U.S. application Ser. No. 10/622,932, incorporated by reference herein.

IV. Pharmaceutical Compositions and Pharmaceutical Administration

A. Compositions and Administration

Antibodies, antibody-portions, and other TNFα inhibitors for use in the methods of the invention, may be incorporated into pharmaceutical compositions suitable for administration to a subject having erosive polyarthritis. Typically, the pharmaceutical composition comprises an antibody, antibody portion, or other TNFα inhibitor of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In one embodiment, the antibody or other TNFα inhibitor is administered by intravenous infusion or injection. In another embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Supplementary active compounds can also be incorporated into the compositions. In certain embodiments, an antibody or antibody portion for use in the methods of the invention is coformulated with and/or coadministered with one or more additional therapeutic agents, including an erosive polyarthritis inhibitor or antagonist. For example, an anti-hTNFα antibody or antibody portion of the invention may be coformulated and/or coadministered with one or more additional antibodies that bind other targets associated with erosive polyarthritis (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexanylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

In one embodiment, the invention includes pharmaceutical compositions comprising an effective amount of a TNFα inhibitor and a pharmaceutically acceptable carrier, wherein the effective amount of the TNFα inhibitor may be effective to treat erosive polyarthritis. In one embodiment, the antibody or antibody portion for use in the methods of the invention is incorporated into a pharmaceutical formulation as described in PCT/IB03/04502 and U.S. application Ser. No. 10/222,140, incorporated by reference herein. This formulation includes a concentration 50 mg/ml of the antibody D2E7, wherein one pre-filled syringe contains 40 mg of antibody for subcutaneous injection. In another embodiment, the formulation of the invention includes D2E7.

The antibodies, antibody-portions, and other TNFα inhibitors of the present invention can be administered by a variety of methods known in the art, although for many therapeutic applications, the preferred route/mode of administration is subcutaneous injection. In another embodiment, administration is via intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

TNFα antibodies may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. application Ser. No. 10/222,140, incorporated by reference herein, are used to treat erosive polyarthritis using treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In one embodiment, the invention provides a single dose method for treating erosive polyarthritis, comprising administering to a subject in need thereof a single dose of a TNFα inhibitor, such as a human antibody. In one embodiment, the TNFα inhibitor is the anti-TNFα antibody adalimumab. The single dose of TNFα inhibitor can be any therapeutically or prophylactically effective amount. In one embodiment, a subject is administered either a 20 mg, a 40 mg, or an 80 mg single dose of adalimumab (also referred to as D2E7). The single dose may be administered through any route, including, for example, subcutaneous administration. Biweekly dosing regimens can be used to treat erosive polyarthritis and are further described in U.S. application Ser. No. 10/163,657. Multiple variable dose methods of treatment or prevention can also be used to treat erosive polyarthritis, and are further described in PCT appin. no. PCT/US05/012007.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. It should also be noted that the invention pertains to methods of treatment of erosive polyarthritis including acute management and chronic management of the disease.

The invention also pertains to packaged pharmaceutical compositions or kits for administering the anti-TNF antibodies of the invention for the treatment of erosive polyarthritis. In one embodiment of the invention, the kit comprises a TNFα inhibitor, such as an antibody, a second pharmaceutical composition comprising an additional therapeutic agent, and instructions for administration for treatment of erosive polyarthritis. The instructions may describe how, e.g., subcutaneously, and when, e.g., at week 0 and week 2, the different doses of TNFα inhibitor and/or the additional therapeutic agent shall be administered to a subject for treatment.

Another aspect of the invention pertains to kits containing a pharmaceutical composition comprising an anti-TNFα antibody and a pharmaceutically acceptable carrier and one or more pharmaceutical compositions each comprising a drug useful for treating erosive polyarthritis and a pharmaceutically acceptable carrier. Alternatively, the kit comprises a single pharmaceutical composition comprising an anti-TNFα antibody, one or more drugs useful for treating erosive polyarthritis and a pharmaceutically acceptable carrier. The kits contain instructions for dosing of the pharmaceutical compositions for the treatment of erosive polyarthritis.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

B. Additional Therapeutic Agents

The invention also describes methods of treating erosive polyarthritis comprising administering a TNFα inhibitor in combination with an additional therapeutic agent. The invention also pertains to pharmaceutical compositions and methods of use thereof for the treatment of erosive polyarthritis in combination with an additional therapeutic agent. The pharmaceutical compositions comprise a first agent that treats erosive polyarthritis. The pharmaceutical composition also may comprise a second agent that is an active pharmaceutical ingredient; that is, the second agent is therapeutic and its function is beyond that of an inactive ingredient, such as a pharmaceutical carrier, preservative, diluent, or buffer. In one embodiment, the second agent may be useful in treating or preventing erosive polyarthritis. In another embodiment, the second agent may diminish or treat at least one symptom(s) associated with the disorder which is associated with erosive polyarthritis, e.g., psoriatic arthritis. In yet another embodiment, the additional agent is useful for the treatment of both erosive polyarthritis and the additional disorder. The first and second agents may exert their biological effects by similar or unrelated mechanisms of action; or either one or both of the first and second agents may exert their biological effects by a multiplicity of mechanisms of action. A pharmaceutical composition may also comprise a third compound, or even more yet, wherein the third (and fourth, etc.) compound has the same characteristics of a second agent.

It should be understood that the pharmaceutical compositions described herein may have the first and second, third, or additional agents in the same pharmaceutically acceptable carrier or in a different pharmaceutically acceptable carrier for each described embodiment. It further should be understood that the first, second, third and additional agent may be administered simultaneously or sequentially within described embodiments. Alternatively, a first and second agent may be administered simultaneously, and a third or additional agent may be administered before or after the first two agents.

The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

Supplementary active compounds can also be incorporated into the compositions. In certain embodiments, an antibody or antibody portion of the invention is coformulated with and/or coadministered with one or more additional therapeutic agents that are useful for treating erosive polyarthritis. For example, an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies or other TNFα inhibitors of the invention may be used in combination with two or more of the foregoing therapeutic agents. Such combination therapies may advantageously utilize lower dosages of the administered therapeutic agents, thus avoiding possible toxicities or complications associated with the various monotherapies.

TNFα inhibitors, e.g., a TNFα antibody, or antigen-binding portion thereof, described herein may be used in combination with additional therapeutic agents for the treatment erosive polyarthritis. Preferably the other drug is a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine.

Nonlimiting additional agents which can also be used in combination with a TNFα inhibitor, e.g., a TNFα antibody, or antigen-binding portion thereof, to treat erosive polyarthritis include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., Arthritis & Rheumatism (1994) Vol. 37, 5295; J. Invest. Med. (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., Arthritis & Rheumatism (1995) Vol. 38, S185); DAB 486-IL-2 and/or DAB 389-IL-2 (IL-2 fusion proteins; Seragen; see e.g., Arthritis & Rheumatism (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., Arthritis & Rheumatism (1996) Vol. 39, No. 9 (supplement), S284; Amer. J. Physiol. —Heart and Circulatory Physiology (1995) Vol. 268, pp. 37-42); R973401 (phosphodiesterase Type IV inhibitor; see e.g., Arthritis & Rheumatism (1996) Vol. 39, No. 9 (supplement), S282); MK-966 (COX-2 Inhibitor; see e.g., Arthritis & Rheumatism (1996) Vol. 39, No. 9 (supplement), S81); Iloprost (see e.g., Arthritis & Rheumatism (1996) Vol. 39, No. 9 (supplement), S82); methotrexate; thalidomide (see e.g., Arthritis & Rheumatism (1996) Vol. 39, No. 9 (supplement), S282) and thalidomide-related drugs (e.g., Celgen); leflunomide (anti-inflammatory and cytokine inhibitor; see e.g., Arthritis & Rheumatism (1996) Vol. 39, No. 9 (supplement), S131; Inflammation Research (1996) Vol. 45, pp. 103-107); tranexamic acid (inhibitor of plasminogen activation; see e.g., Arthritis & Rheumatism (1996) Vol. 39, No. 9 (supplement), S284); T-614 (cytokine inhibitor; see e.g., Arthritis & Rheumatism (1996) Vol. 39, No. 9 (supplement), S282); prostaglandin E1 (see e.g., Arthritis & Rheumatism (1996) Vol. 39, No. 9 (supplement), S282); Tenidap (non-steroidal anti-inflammatory drug; see e.g., Arthritis & Rheumatism (1996) Vol. 39, No. 9 (supplement), S280); Naproxen (non-steroidal anti-inflammatory drug; see e.g., Neuro Report (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., Arthritis & Rheumatism (1996) Vol. 39, No. 9 (supplement), S281); Azathioprine (see e.g., Arthritis & Rheumatism (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitos of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39, No. 9 (supplement), S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxy-nucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents. Any of the above-mentioned agents can be administered in combination with the TNFα ☐inhibitor, including a TNFα ☐ antibody, to treat erosive polyarthritis or to inhibit radiographic progression of joint disease.

In one embodiment, the TNFα inhibitor, e.g., a TNFα antibody, or antigen-binding portion thereof, is administered in combination with one of the following agents for the treatment of rheumatoid arthritis: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, the TNFα antibody of the invention is administered for the treatment of a TNFα related disorder in combination with one of the above mentioned agents for the treatment of rheumatoid arthritis.

In one embodiment, the TNFα inhibitor, e.g., a TNFα antibody, or antigen-binding portion thereof, is used in combination with a drug used to treat Crohn's disease or a Crohn's-related disorder. Examples of therapeutic agents which can be used to treat Crohn's include mesalamine, prednisone, azathioprine, mercaptopurine, infliximab, budesonide, sulfasalazine, methylprednisolone sod succ, diphenoxylate/atrop sulf, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab, and interferon-gamma.

In one embodiment, the TNFα inhibitor, e.g., a TNFα antibody, or antigen-binding portion thereof, is administered in combination with an agent which is commonly used to treat spondyloarthropathies, such as AS. Examples of such agents include nonsteroidal, anti-inflammatory drugs (NSAIDs), COX 2 inhibitors, including Celebrex®, Vioxx®, and Bextra®, and etoricoxib. Physiotherapy is also commonly used to treat spondyloarthropathies, usually in conjunction with non-steoidal inflammatory drugs.

In one embodiment, the TNFα inhibitor, e.g., a TNFα antibody, or antigen-binding portion thereof, is administered in combination with an additional therapeutic agent to treat ankylosing spondylitis. Examples of agents which can be used to reduce or inhibit the symptoms of ankylosing spondylitis include ibuprofen, diclofenac and misoprostol, naproxen, meloxicam, indomethacin, diclofenac, celecoxib, rofecoxib, sulfasalazine, prednisone, methotrexate, azathioprine, minocyclin, prednisone, etanercept, and infliximab.

In one embodiment, the TNFα inhibitor, e.g., a TNFα antibody, or antigen-binding portion thereof, is administered in combination with an additional therapeutic agent to treat psoriatic arthritis. Examples of agents which can be used to reduce or inhibit the symptoms of psoriatic arthritis include methotrexate; etanercept; rofecoxib; celecoxib; folic acid; sulfasalazine; naproxen; leflunomide; methylprednisolone acetate; indomethacin; hydroxychloroquine sulfate; sulindac; prednisone; betamethasone diprop augmented; infliximab; methotrexate; folate; triamcinolone acetonide; diclofenac; dimethylsulfoxide; piroxicam; diclofenac sodium; ketoprofen; meloxicam; prednisone; methylprednisolone; nabumetone; tolmetin sodium; calcipotriene; cyclosporine; diclofenac; sodium/misoprostol; fluocinonide; glucosamine sulfate; gold sodium thiomalate; hydrocodone; bitartrate/apap; ibuprofen; risedronate sodium; sulfadiazine; thioguanine; valdecoxib; alefacept; and efalizumab.

In one embodiment, the TNFα inhibitor, e.g., a TNFα antibody, or antigen-binding portion thereof, is administered in combination with topical corticosteroids, vitamin D analogs, and topical or oral retinoids, or combinations thereof, for the treatment of psoriasis. In addition, the TNFα antibody of the invention is administered in combination with one of the following agents for the treatment of psoriasis: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, alefacept, efalizumab, tacrolimus, pimecrolimus, PUVA, UVB, and sulfasalazine.

An antibody, antibody portion, or other TNFα inhibitor, e.g., a TNFα antibody, or antigen-binding portion thereof, may be used in combination with other agents to treat skin conditions. For example, an antibody, antibody portion, or other TNFα inhibitor of the invention is combined with PUVA therapy. PUVA is a combination of psoralen (P) and long-wave ultraviolet radiation (UVA) that is used to treat many different skin conditions. The antibodies, antibody portions, or other TNFα inhibitors of the invention can also be combined with pimecrolimus. In another embodiment, the antibodies of the invention are used to treat psoriasis, wherein the antibodies are administered in combination with tacrolimus. In a further embodiment, tacrolimus and TNFα inhibitors are administered in combination with methotrexate and/or cyclosporine. In still another embodiment, the TNFα inhibitor of the invention is administered with excimer laser treatment for treating psoriasis.

Nonlimiting examples of other therapeutic agents with which a TNFα inhibitor, e.g., a TNFα antibody, or antigen-binding portion thereof, can be combined to treat a skin or nail disorder include UVA and UVB phototherapy. Other nonlimiting examples which can be used in combination with a TNFα inhibitor include anti-IL-12 and anti-IL-18 therapeutic agents, including antibodies.

Any one of the above-mentioned therapeutic agents, alone or in combination therewith, can be administered to a subject suffering from erosive polyarthritis, in combination with the TNFα a ☐inhibitor, including a TNFα ☐ antibody, or antigen-binding portion thereof. A TNFα antibody, or antigen-binding portion thereof, may be used in combination with additional therapeutic agents known to be effective at acute management of subjects with erosive polyarthritis. A TNFα antibody, or antigen-binding portion thereof, may also be used in combination with additional therapeutic agents known to be effective at management of subjects with erosive polyarthritis.

This invention is further illustrated by the following example which should not be construed as limiting. The contents of all references, patents and published patent applications cited throughout this application are incorporated herein by reference.

EXAMPLE

Treatment of Erosive Polyarthritis in Patients with Psoriatic Arthritis Using a TNF Inhibitor Erosive polyarthritis occurs in a substantial proportion of patients with psoriatic arthritis (PsA). Traditional, non-biologic DMARDs have not been shown to effectively inhibit the radiographic progression of joint damage in this disease.

The following study was performed to evaluate the efficacy of a TNF inhibitor, more specifically the anti-TNF antibody adalimumab, for the treatment of erosive polyarthritis. The study was performed to evaluate whether adalimumab was effective at inhibiting the radiographic progression of joint disease associated with erosive polyarthritis in patients with moderate to severe PsA.

A 24-week, double-blind, randomized, placebo-controlled trial of adult patients with moderate to severely active PsA (≥3 swollen and ≥3 tender joints) who had failed NSAID therapy was performed. Patients were stratified according to methotrexate (MTX) use (yes/no) and degree of psoriasis (<3% or ≥3% Body Surface Area [BSA]). In addition to having ≥3 swollen and ≥3 tender joints, inclusion criteria included an inadequate response to NSAID therapy, a history of psoriasis, and age ≥18 years. Exclusion criteria included the following: prior anti-TNF therapy, alefacept within 12 weeks prior to study entry, other biologics within 6 weeks prior to study entry, systemic therapies for psoriasis within 4 weeks prior to study entry, and phototherapy and topicals within 2 weeks prior to study entry.

Patients were randomized to receive either adalimumab 40 mg or placebo subcutaneously every other week (eow) for 24 weeks. Patients who completed the 24-week trial were eligible to enroll in an open-label extension (OLE) study, in which all patients received adalimumab eow. After 12 weeks of treatment with open label therapy, patients failing to meet pre-specified criteria were eligible to receive 40 mg weekly.

Figure 1A:
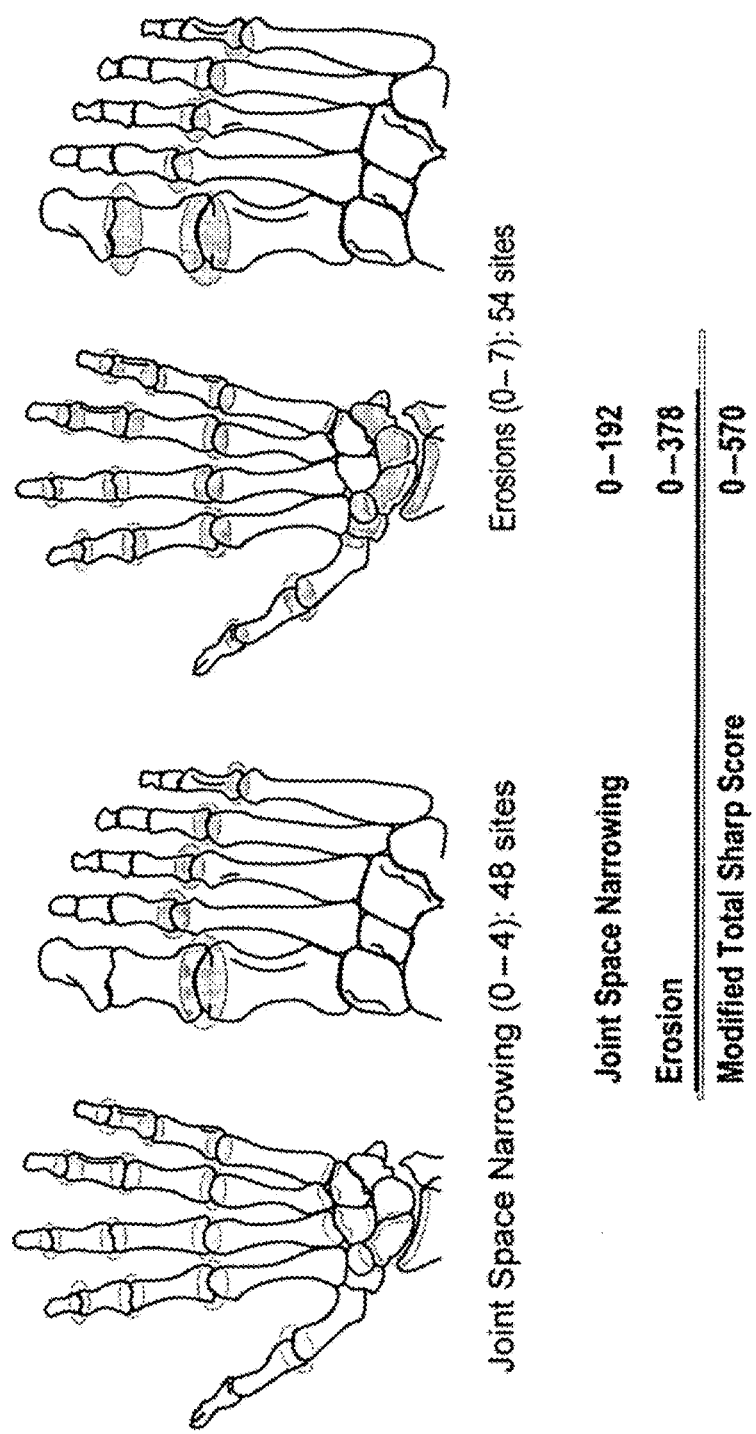
FIGS. 1a and 1b show a diagram of the modified total sharp score (mTSS) (FIG. 1a) and radiographic findings associated with PsA (FIG. 1b).
Figure 1B:
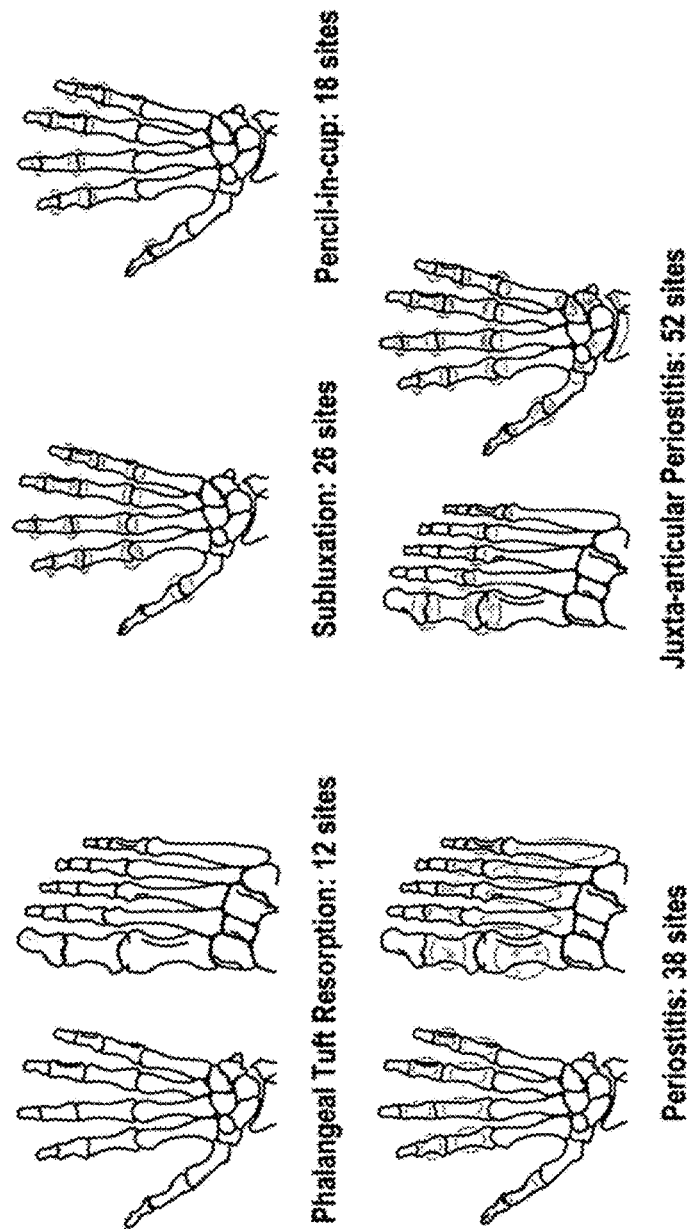

Radiographic assessments were performed during both the blinded portion (Weeks 0 and 24) and the open-label portion (Week 48). Radiographs of the hands and feet were assessed by a modified total Sharp score (mTSS) in which additional joints typically involved in PsA were added, and, to better quantify the significant osteolysis that occurs in PsA, the numerical scales were expanded. The mTSS was determined by combining the joint space narrowing score (0-192) and the erosion score (0-378), as shown in FIG. 1a. Clinical findings associated with PsA, e.g., pencil-in-cup changes, were also evaluated. Diagrams of the mTSS and the radiographic findings associated with PsA used in this study are shown in FIGS. 1a and 1b, respectively.

The radiograph reading procedure included the following. All films were read by two independent readers who were blinded to treatment and film order. Read number 1 was an evaluation of baseline and week 24 films. Read number 2 was an evaluation of baseline, week 24, and week 48 films.

Several sensitivity analyses were utilized to assess the impact of missing radiographs (imputation of zero change, worst rank change, $50^{th}/75^{th}$ percentile change based on patients with similar baseline scores, and linear extrapolation when multiple radiographs were available).

Week 24 analysis included the following: inclusion in the week 24 analysis required both baseline and week 24 films, where at least 50% of the joints were evaluable. Week 48 analysis included the following: All patients from the 24 week analysis were included in the week 48 analysis. If the week 48 film was not available (or <50% of the joints evaluable), then the following imputation was performed: if originally randomized to placebo, a change of 0 was imputed; and if originally randomized to adalimumab, linear extrapolation using first two films was conducted.

Baseline demographics and disease severity characteristics were consistent with moderate to severe PsA and were well-matched between treatment arms (adalimumab N=151, placebo N=162; mean±SD): age 49.0±11.8 yrs; duration of PsA 9.5±8.5 yrs; SJC (76) 14±12; TJC (78) 25±18; HAQ 1.0±0.6; mTSS 20.8±40.9; 51% were taking concomitant methotrexate. Of the total, 296 patients had X-rays at baseline and Week 24, and 265 patients also had X-rays at Week 48.

As reported in previous studies, the ACR20, 50, and 70 responses and the PASI 50, 75, and 90 responses for adalimumab-treated patients at week 24 were significantly better than placebo. ACR and PASI responses at week 24 are shown below in tables 1 and 2 (all results p≤0.001 placebo vs. adalimumab):

TABLE 1

| ACR response: % of patients | | | |
|---|---|---|---|
| | ACR20 | ACR50 | ACR70 |
| Placebo (N = 162) | 15 | 6 | 1 |
| Adalimumab (N = 151) | 57 | 39 | 23 |

TABLE 2

PASI response: % of patients

|  | PASI 50 | PASI 75 | PASI 90 |
|---|---|---|---|
| Placebo (N = 69) | 12 | 1 | 0 |
| Adalimumab (N = 69) | 75 | 59 | 42 |

Figure 2:
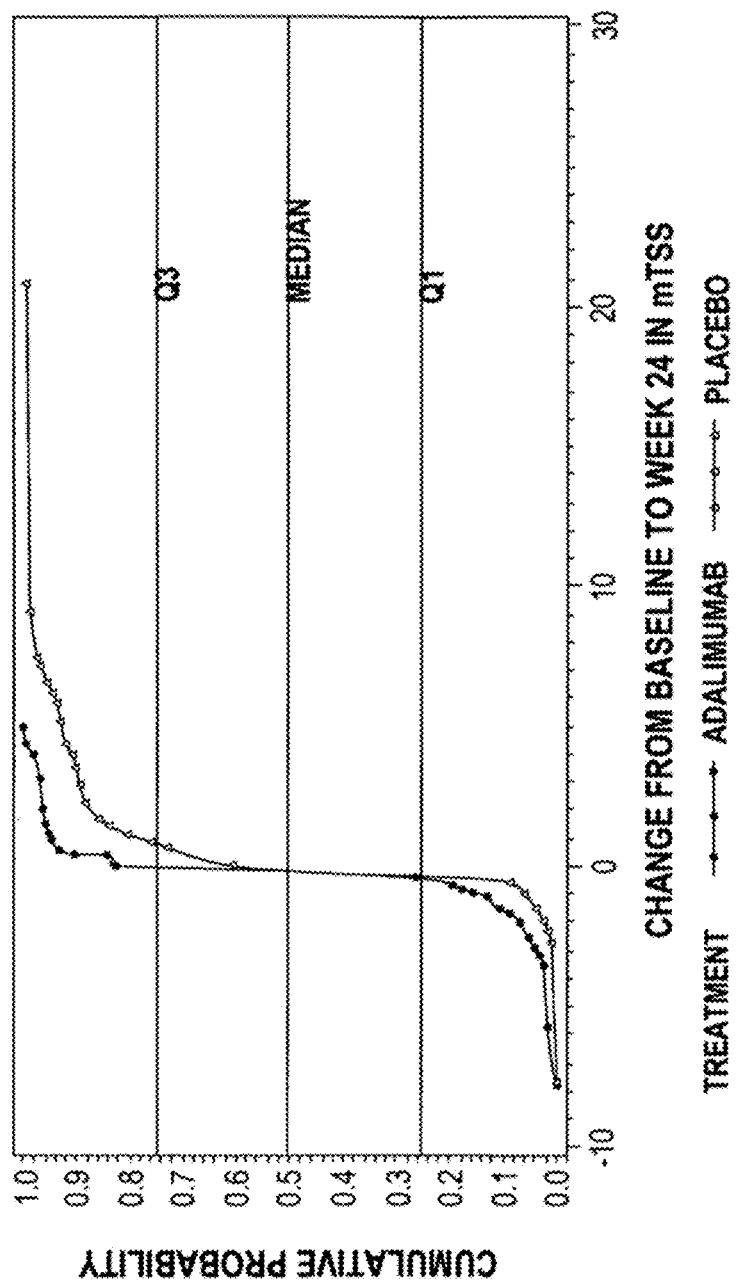
FIG. 2 shows a cumulative distribution function plot of modified Total Sharps Score (mTSS). The graph shows the change in baseline to Week 24 for subjects with both baseline and Week 24 radiographic films.

During the blinded study period (24 wks), adalimumab patients had significantly less progression in mTSS than placebo patients (mean change in mTSS −0.2 vs. 1.0, p<0.001, ranked ANCOVA). Statistical significance was maintained in all sensitivity analyses. FIG. 2 shows the distribution of mTSS scores which demonstrates that fewer patients treated with adalimumab had an increase in structural damage during 24 weeks of treatment compared with placebo. The difference in distribution was observed by looking at mean scores at week 24 and the number and percentage of patients who had an increase in Sharp score during the study (see Table 3). Approximately three times as many placebo-treated patients had an increase in mTSS (>0.5 units) than adalimumab-treated patients during the first 24 weeks of treatment.

TABLE 3

Change* in Modified Total Sharp Score at Week 24

|  | Placebo N = 152 n (%) | Adalimumab N = 144 n (%) |
|---|---|---|
| Decrease in Sharp Score | 8 (5.3%) | 27 (18.8%) |
| No change in Sharp Score | 100 (65.8%) | 104 (72.2%) |
| Increase in Sharp Score | 44 (28.9%) | 13 (9.0%) | p ≤ 0.001 placebo vs. adalimumab using CMH test
*Change defined as >0.5 units in mTSS Score Statistically significant differences were observed between adalimumab and placebo treated subjects for both erosion scores and joint narrowing scores (p≤0.001 using a ranked ANACOVA). At Week 24, the change in erosion scores (change from baseline) were 0.6 for placebo patients and 0.0 for adalimumab patients (p≤0.001, ranked ANCOVA), and the change in joint space narrowing scores (change from baseline) were 0.4 for placebo patients and −0.2 for adalimumab patients (p<0.001, ranked ANCOVA).

Sensitivity analyses to account for missing patients films were performed and results maintained statistical significance with all analyses. Post-hoc sensitivity analyses excluding feet and DIPs were as follows: one analysis was run excluding feet and DIPs and a second analysis was run excluding all DIP joints. Statistical significance was maintained in both analyses.

Figures 3A, 3B:
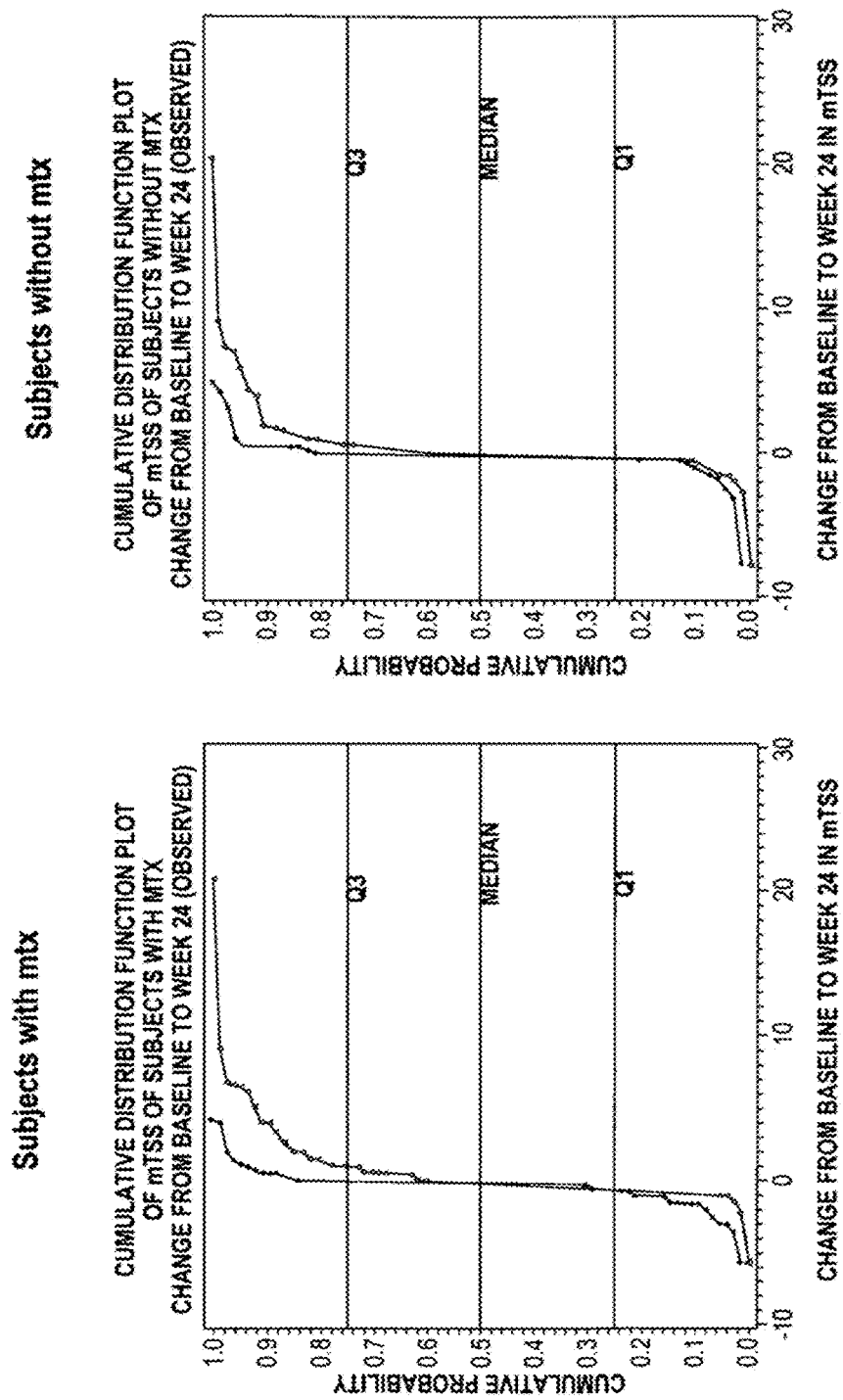
FIGS. 3a and 3b show cumulative distribution function plots of mTSS of subjects with (FIG. 3a) and without (FIG. 3b) methotrexate (mtx).

Statistically significant differences were observed between adalimumab and placebo treated subjects regardless of whether concomitant MTX was being used. Mean differences were slightly higher for patients taking concomitant MTX. Patients on monotherapy showed a change from baseline of −0.1 in adalimumab (n=68) vs. 0.9 for placebo (n=74) (p≤0.001 using a ranked ANACOVA). Patients on concomitant MTX showed a change from baseline of −0.3 in adalimumab (n=76) vs. 1.2 for placebo (n=78) (p≤0.001 using a ranked ANACOVA). FIGS. 3a and 3b show cumulative distribution function plots of mTSS of subjects with and without MTX.

Figure 4:
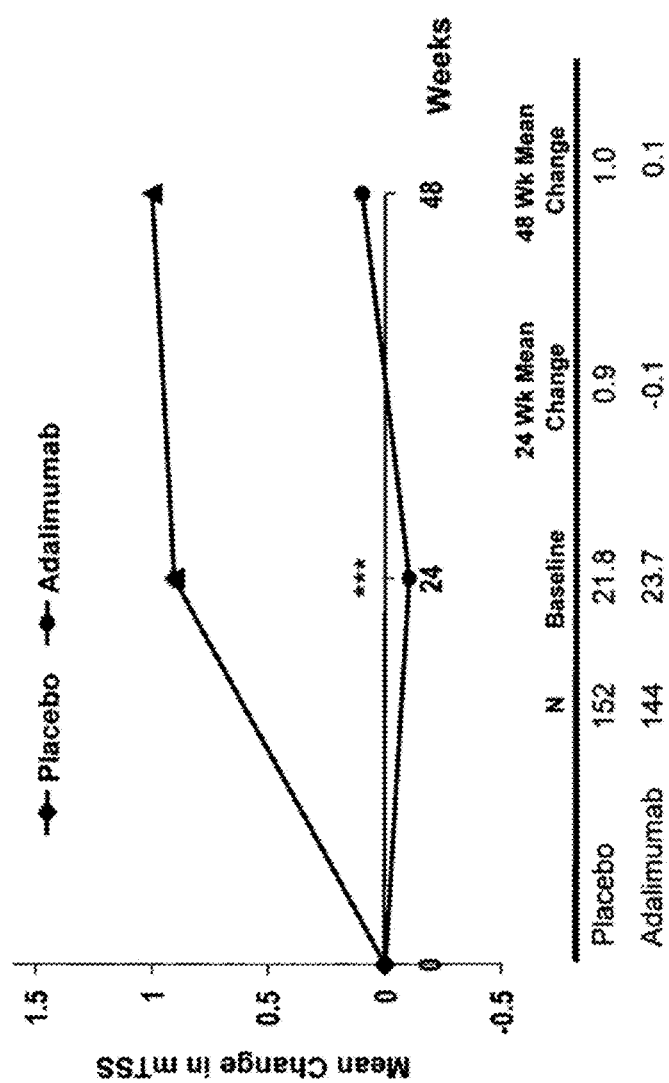
FIG. 4 shows a graph of the mean change in mTSS at Week 48.

Analysis of 48-week radiographs demonstrated that the lack of progression (lack of changes in mTSS) observed at Week 24 was maintained to Week 48 in adalimumab patients (see FIG. 4). Patients treated with placebo for 24 weeks did not have radiographic progression of disease during the open-label period. Neither treatment arm demonstrated significant progression in PsA-associated features. The prevalence of PsA-associated findings are shown in Table 4. No significant difference was found between groups at baseline, and no significant progression was found in either group during the 24-week study.

TABLE 4

Prevalence of PsA-associated findings

|  | All patients (N = 313) n (%) |
|---|---|
| Joint space widening | 38 (12.1%) |
| Gross osteolysis | 60 (19.2%) |
| Subluxation | 49 (15.7%) |
| Pencil-in-cup | 9 (2.9%) |
| Juxta-articular periostitis | 247 (78.9%) |
| Shaft periostitis | 140 (44.7%) |
| Phalangeal tuft resorption | 224 (71.6%) |

Furthermore, adalimumab was generally well-tolerated as reported previously.

Adalimumab was more effective compared with placebo in inhibiting radiographic disease progression over a 24-week period. Adalimumab showed differences versus placebo both in patients taking concomitant methotrexate and in those taking adalimumab as monotherapy. The inhibition of structural damage progression observed in adalimumab-treated patients at 24 weeks was maintained at one year. In conclusion, this study demonstrated that adalimumab was effective in treating erosive polyarthritis and radiographic disease progression over one year in patients who also had moderate to severely active PsA.

D2E7 in Human Subjects with Psoriasis

Patients with moderate to severe chronic plaque psoriasis are selected for the study. None of the patients will have received any psoriasis treatments for at least 4 weeks or any topical treatments for at least 2 weeks before study entry. Doses of D2E7 begin at 40 mg weekly or 40 mg every other week administered by subcutaneous injection.

Patients are examined clinically every 2-4 weeks. Clinical activity of psoriatic skin lesions is evaluated by means of the Psoriasis Area and Severity Index (PASO (Fredriksson and Pettersson (1978) *Dermatologica* 157:238-44) and the Physician's Global Assessment by the same investigator to ensure consistent evaluations. At week 12, the primary end point of proportion of patients achieving at least 75% reduction in PASI score compared to baseline is determined. Pruritus is assessed by using a validated scale. Quality of life assessments are measured using validated instruments, including, but not limited to the DLQI, SF-36, and EQ-5D. Full-body photographs excluding the face are taken at scheduled visits throughout the study.

Skin biopsy specimens are obtained at scheduled intervals during the study to correlate histology and biomarkers in the skin with treatment. A biopsy of normal skin is obtained at baseline for comparison with psoriatic skin.

Multiple-Variable Dose Treatment of Psoriasis With D2E7

A study was performed to determine the efficacy of a multiple-variable dose regimen of D2E7 for treating psoriasis. Efficacy and tolerability of D2E7 in the treatment of patients with moderate to severe chronic plaque psoriasis were evaluated in a randomized, double-blind, placebo-controlled multicenter study.

In this study, one hundred forty-eight adult patients with a diagnosis of moderate to severe psoriasis for at least one year were selected to receive multiple-variable dose treatment. Patients were also selected based on an affected body surface area (BSA) of ≥5%. Subjects were randomized equally to one of three groups (two treatment groups and one placebo).

At baseline (Week 0) patients in both treatment groups received an induction dose of 80 mg of D2E7. Patients in the first treatment group subsequently received a treatment dose of 40 mg of D2E7 at week 1 followed by 40 mg every other week (eow) starting at week 3. Subjects in the second treatment group received an induction dose of 80 mg dose of D2E7 at Week 1 (following the initial 80 mg dose at Week 0) followed by a treatment dose of 40 mg of D2E7 weekly starting at week 2. The placebo group received only the placebo weekly starting at baseline. All treatment was administered subcutaneously (sc) with pre-filled syringes. A summary of the different regimens are described below in Table 5:

TABLE 5

Psoriasis study regimens

| Regimen | Detailed description |
|---|---|
| A | D2E7 80 mg sc administered at Week 0 (baseline); D2E7 40 mg sc every other week administered starting at Week 1 through Week 11, with placebo administered on alternate weeks |
| B | D2E7 80 mg sc administered starting at Week 0 (baseline) and at Week 1 (80/80); D2E7 40 mg sc weekly administered starting at Week 2 through Week 11 |
| C | Placebo sc will be administered at baseline and then weekly through Week 11, with two injections given at Week 1 and Week 1 |

In order to maintain the blind study, all subjects received a total of 2 injections at baseline and week 1. During the remaining period of the study (weeks 2 through 12), subjects received one injection per week. The treatment dose per injection correlated to the dose regimen randomly assigned to each subject.

The PASI of the participants of the multiple-variable dose regimen was determined according to standard methods (see Fredriksson and Pettersson, supra and Marls et al., supra). The primary efficacy endpoint of the study was the percentage of subjects achieving a clinical response as defined by at least a 75% reduction in the PASI score (≥PAST 75) at Week 12.

Secondary efficacy measures included a static Physician's Global Assessment (PGA) of "clear" or "almost clear" at Week 12. PGA was determined according to a seven point scale used to measure the severity of psoriasis at the time of the physician's evaluation. Descriptions of the disease included the following: severe=very marked plaque elevation, scaling, and/or erythema; moderate to severe=marked plaque elevation, scaling, and/or erythema; moderate=moderate plaque elevation, scaling, and/or erythema; mild to moderate=intermediate between moderate and mild; mild=slight plaque elevation, scaling, and/or erythema; almost clear=intermediate between mild and clear; and clear=no signs of psoriasis.

Figure 5:
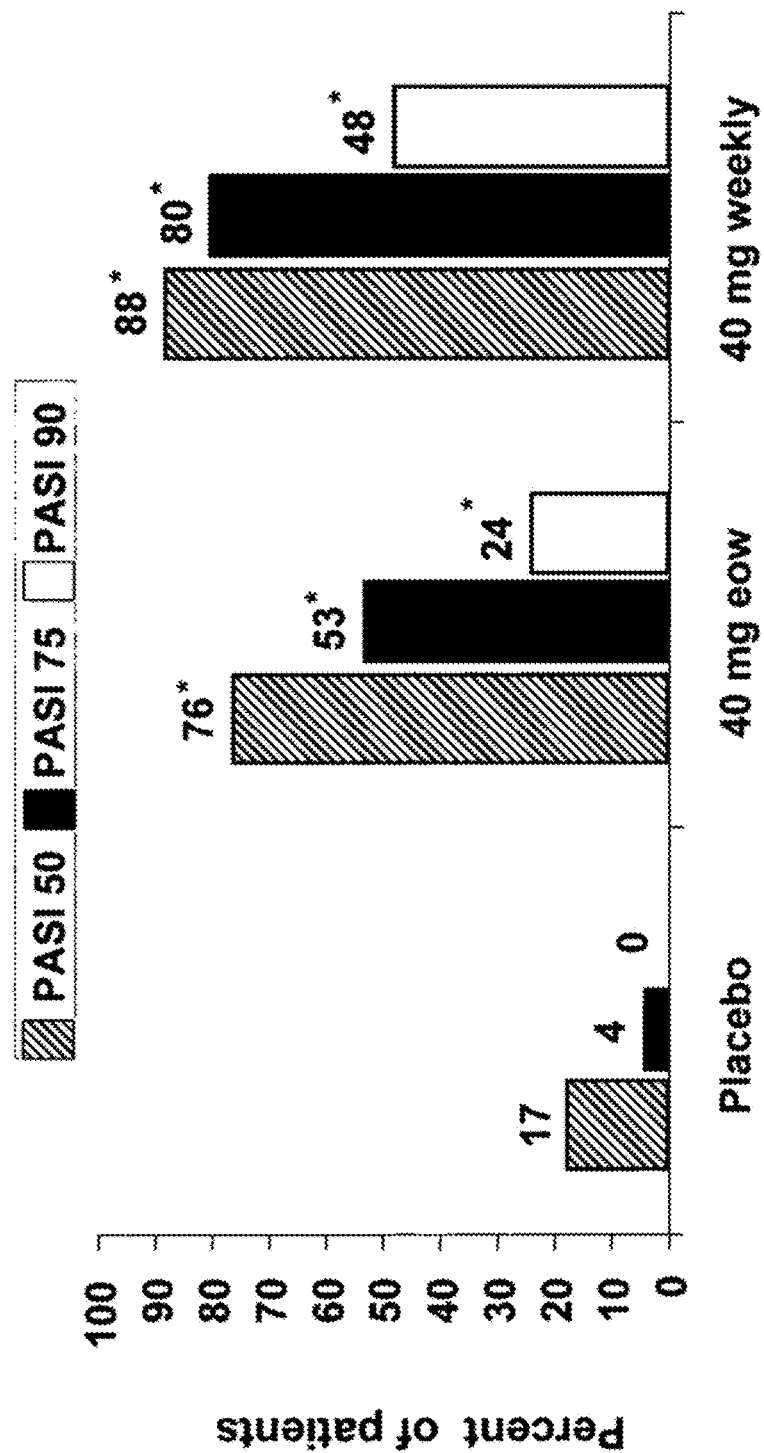
FIG. 5 shows the percentage of psoriasis patients with ≥PAST 50/75/90 response at week 12 following treatment with each multiple variable D2E7 dose and the placebo.

The results show that at Week 12, statistically significantly greater percentages of patients achieved a PASI 75 response or better on D2E7 than those on a placebo treatment. For patients receiving 40 mg treatment dose of D2E7 eow, 53% demonstrated a PASI of 75 or higher. In addition, 80% of patients receiving a 40 mg treatment dose of D2E7 weekly showed a PASI 75 or higher, compared to only 4% of the placebo treatment group ($p<0.001$ vs. placebo). Response rates at Week 12 for both dosing regimens of D2E7 were statistically significantly greater than for placebo, as shown in FIG. 5.

Overall, the mean percentage changes in PASI score for patients on D2E7 multiple-variable dose therapy were statistically significantly greater than placebo. The changes were evident as early as Week 1 after the initial dose, as shown in FIG. 6. At Week 12, 49% of patients on D2E7 receiving 40 mg eow and 76% of patients receiving 40 mg of D2E7 weekly achieved a PGA of "clear" or "almost clear," compared with 2% of placebo patients.

Overall, the mean percentage changes in PASI score for patients on D2E7 multiple-variable dose therapy were statistically significantly greater than placebo. The changes were evident as early as Week 1 after the initial dose, as shown in FIG. 6. At Week 12, 49% of patients on D2E7 receiving 40 mg eow and 76% of patients receiving 40 mg of D2E7 weekly achieved a PGA of "clear" or "almost clear," compared with 2% of placebo patients.

Of the one hundred forty-eight adult patients enrolled in the study, 29% also had a medical history of psoriatic arthritis (PsA). Both doses of D2E7 were effective in the treatment of psoriasis in both patients with and without PsA. Patients with PsA had a similar efficacy response to D2E7 as those without PsA. For both PsA and without PsA subgroups, the percentages of patients achieving a PASI 75 response or better at week 12 was statistically significant for the eow (with PsA, 47%; without PsA, 57%) and weekly treatment arms (with PsA, 58%; without PsA, 87%) compared with placebo. Continued improvements in efficacy were seen through week 24 in the eow arm (with PsA, 53%; without PsA, 70%). Efficacy responses in patients with and without PsA at weeks 12 and 24 are shown in FIGS. 7 and 8, respectively.

In conclusion, D2E7 administered for 12 weeks was effective in the treatment of moderate to severe chronic plaque psoriasis. 53% of patients on 40 mg eow achieved ≥PASI 75, compared with 4% on placebo. 80% of patients on 40 mg weekly achieved ≥PASI 75. 49% and 76% of patients on D2E7 40 mg eow and 40 mg weekly, respectively, were "clear" or "almost clear" of their psoriasis. In addition, D2E7 was equally effective at treating psoriasis patients with and without PsA.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A method for treating moderate to severe chronic plaque psoriasis, comprising subcutaneously administering to an adult patient having moderate to severe chronic plaque psoriasis an initial dose of 80 mg of adalimumab, followed by 40 mg of adalimumab every other week starting one week after said first dosing, wherein the patient achieves at least Psoriasis Area and Severity Index (PASI) 75 response at week 12 of the treatment.

2. The method of claim 1, wherein at least 5% body surface area (BSA) of the patient is affected by the moderate to severe chronic plaque psoriasis.

3. The method of claim 1, wherein adalimumab is comprised in pre-filled syringes for subcutaneous injection.

4. The method of claim 1, wherein adalimumab is formulated in a pharmaceutical composition and at a concentration of 50 mg/ml.

5. The method of claim 3, wherein adalimumab is formulated in a pharmaceutical composition and at a concentration of 50 mg/ml.

6. The method of claim 2, wherein adalimumab is comprised in pre-filled syringes for subcutaneous injection.

7. The method of claim 2, wherein adalimumab is formulated in a pharmaceutical composition and at a concentration of 50 mg/ml.

8. The method of claim 6, wherein adalimumab is formulated in a pharmaceutical composition and at a concentration of 50 mg/ml.

9. A method for treating moderate to severe chronic plaque psoriasis, comprising subcutaneously administering to an adult patient having moderate to severe chronic plaque psoriasis an initial dose of 80 mg of adalimumab, followed by 40 mg of adalimumab every other week starting one week after said first dosing.

10. The method of claim 9, wherein at least 5% body surface area (BSA) of the patient is affected by the moderate to severe chronic plaque psoriasis.

11. The method of claim 9, wherein adalimumab is comprised in pre-filled syringes for subcutaneous injection.

12. The method of claim 9, wherein adalimumab is formulated in a pharmaceutical composition and at a concentration of 50 mg/ml.

13. The method of claim 11, wherein adalimumab is formulated in a pharmaceutical composition and at a concentration of 50 mg/ml.

14. The method of claim 10, wherein adalimumab is comprised in pre-filled syringes for subcutaneous injection.

15. The method of claim 10, wherein adalimumab is formulated in a pharmaceutical composition and at a concentration of 50 mg/ml.

16. The method of claim 15, wherein adalimumab is formulated in a pharmaceutical composition and at a concentration of 50 mg/ml.

\* \* \* \* \*